US010940333B2

(12) United States Patent
Thieme et al.

(10) Patent No.: US 10,940,333 B2
(45) Date of Patent: Mar. 9, 2021

(54) SYSTEMS, METHODS, AND DEVICES FOR RADIATION BEAM ALIGNMENT AND RADIATION BEAM MEASUREMENTS USING ELECTRONIC PORTAL IMAGING DEVICES

(71) Applicant: Varian Medical Systems International AG, Steinhausen (CH)

(72) Inventors: Stefan Thieme, Windisch (CH); Mathias Lehmann, Zurich (CH)

(73) Assignee: VARIAN MEDICAL SYSTEMS INTERNATIONAL AG, Steinhausen (CH)

( * ) Notice: Subject to any disclaimer, the term of this patent is extended or adjusted under 35 U.S.C. 154(b) by 260 days.

(21) Appl. No.: 15/994,077

(22) Filed: May 31, 2018

(65) Prior Publication Data
US 2018/0272155 A1    Sep. 27, 2018

Related U.S. Application Data

(62) Division of application No. 15/017,280, filed on Feb. 5, 2016, now Pat. No. 10,022,564.

(51) Int. Cl.
*A61N 5/10* (2006.01)
*A61B 6/00* (2006.01)
*A61B 6/06* (2006.01)

(52) U.S. Cl.
CPC .......... *A61N 5/1075* (2013.01); *A61B 6/4241* (2013.01); *A61B 6/4258* (2013.01); *A61B 6/5258* (2013.01); *A61N 5/1045* (2013.01); *A61N 5/1049* (2013.01); *A61B 6/06* (2013.01); *A61B 6/4233* (2013.01); *A61N 2005/1054* (2013.01); *A61N 2005/1074* (2013.01); *A61N 2005/1089* (2013.01)

(58) Field of Classification Search
CPC ...... A61N 5/10; A61N 5/1052; A61N 5/1075; A61N 2005/1052
See application file for complete search history.

(56) References Cited

U.S. PATENT DOCUMENTS

| 5,109,276 A | * | 4/1992 | Nudelman | ......... A61B 1/00193 |
| | | | | 348/47 |
| 6,094,152 A | | 7/2000 | Cheng | |
| 7,453,976 B1 | * | 11/2008 | Yin | ........................ A61B 6/032 |
| | | | | 378/65 |
| 7,486,983 B2 | | 2/2009 | Ghelmansarai et al. | |
| (Continued) | | | | |

FOREIGN PATENT DOCUMENTS

| CN | 102939607 A | 2/2013 |
| CN | 103458967 A | 12/2013 |
| (Continued) | | |

OTHER PUBLICATIONS

Office Action dated Mar. 28, 2019, in European Patent Application No. 17153499.3.
(Continued)

*Primary Examiner* — Samuel G Gilbert
(74) *Attorney, Agent, or Firm* — SGPatents PLLC

(57) ABSTRACT

Systems and methods for using electronic portal imaging devices (EPIDs) as absolute radiation beam measuring devices and as radiation beam alignment devices without implementation of elaborate and complex calibration procedures.

20 Claims, 18 Drawing Sheets

(56) References Cited

U.S. PATENT DOCUMENTS

| 7,594,753 | B2 | 9/2009 | Main et al. |
| 8,049,176 | B1 * | 11/2011 | Majewski ............ A61N 5/1049 250/363.05 |
| 8,130,905 | B1 | 3/2012 | Nelms |
| 2007/0237304 | A1 | 10/2007 | Nelson |
| 2009/0250618 | A1 | 10/2009 | Simon |
| 2012/0014618 | A1 | 1/2012 | Sun et al. |
| 2012/0095329 | A1 | 4/2012 | Kamiya |
| 2015/0352376 | A1 | 12/2015 | Wiggers et al. |

FOREIGN PATENT DOCUMENTS

| EP | 2 837 406 A1 | 2/2015 |
| EP | 2 865 419 A1 | 4/2015 |
| WO | WO 2013/119887 A1 | 8/2013 |
| WO | WO 2014/120423 A1 | 8/2014 |

OTHER PUBLICATIONS

Chinese Office Action dated Jun. 11, 2019, in Chinese Patent Application No. 201710067313.2.

Georg et al., "Current status and future perspective of flattening filter free photon beams," Med. Phys., 38 (3), Mar. 2011, pp. 1280-1293.

Nicolini et al., "GLAaS: An absolute dose calibration algorithm for an amorphous silicon portal image. Applications to IMRT verifications," Med. Phys., 33 (8), Aug. 2006, pp. 2839-2851.

Esch et al., "The use of an aSi-based EPID for routine absolute dosimetric pre-treatment verification of dynamic IMRT fields," Radiotherapy and Oncology, 71, 2004, pp. 223-234.

Herman et al., "Clinical use of electronic imaging: Report of AAPM radiation therapy committee task group 58," Med. Phys., 28 (5), May 2001, pp. 712-737.

Yousif et al., "Performance evaluation of the Siemens Electronics portal Imaging device for IMRT plan verification," International Journal of Medical Physics, Clinical Engineering and Radiation Oncology, 2015, 4, pp. 215-223.

Nelms et al., "Evaluation of a fast method of EPID-based dosimetry for intensity-modulated radiation therapy," Journal of Applied Clinical Physics, vol. 11, No. 2, Spring 2010.

Boriano et al., "A new approach for the pixel map sensitivity (PMS) evaluation of an electronic portal imaging device (EPID)," Journal of Applied Clinical Physics, vol. 14, No. 6, 2013.

Extended European Search Report dated Jul. 21, 2017, in European Application No. 17153499.3.

Partial European Search Report dated Apr. 3, 2017, in European Application No. 17153499.3.

Chinese Office Action dated Jan. 16, 2019, in Chinese Patent Application No. 201710067313.2.

European Examination Report dated Jun. 1, 2018, in European Application No. 17153499.3.

* cited by examiner

SYSTEMS, METHODS, AND DEVICES FOR RADIATION BEAM ALIGNMENT AND RADIATION BEAM MEASUREMENTS USING ELECTRONIC PORTAL IMAGING DEVICES

FIELD

The present disclosure relates generally to radiation therapy, and more specifically to systems and methods for using electronic portal imaging devices (EPIDs) as radiation beam measuring devices and as radiation beam alignment devices without the need for implementing elaborate calibration processes.

BACKGROUND

In radiosurgery or radiotherapy (collectively referred to as radiation therapy) very intense and precisely collimated doses of radiation are delivered to a target region (volume of tumorous tissue) in the body of a patient in order to treat or destroy tumors or other lesions such as blood clots, cysts, aneurysms or inflammatory masses, for example. The goal of radiation therapy is to accurately deliver a prescribed radiation dose to the tumor/lesion and spare the surrounding healthy tissue. The geometric accuracy of patient positioning relative to the treatment beam, as well as the location and amount of dose delivered to the patient is therefore important. There are a number of factors that could affect geometric and dose delivery accuracy, such as, incorrect patient alignment relative to the treatment beam, misalignment of the light field versus radiation field, shift of the skin marker, patient movement, etc.

Because the radiation dose amount and dose placement need to be sufficiently controlled for accurate patient treatment, the radiation therapy machine itself needs to be properly tuned at the outset (on the production floor), and then continuously monitored through periodic checks, such as, during initial installation or during routine usage of the machine by the customer, to ensure that the system is operating within appropriate and expected parameters and standards.

Electronic portal imaging devices (EPIDs) were previously introduced to verify patient position. Thus, their primary use was for patient localization via portal imaging. However, due to their online efficiency and data density, portal imagers/MV EPIDs have also received attention as quality assurance (QA) devices. More recently, EPIDs have been employed for a variety of applications, including patient dosimetry and quality assurance (QA), to verify the treatment beams. Thus, the EPIDs have applications as imaging devices in machine-specific and patient-specific quality assurance (QA) and commissioning and calibration processes.

With the potential benefits of high data density and high resolution for EPID-based QA, there are also inherent problems associated with EPID quality assurance (QA). For example, EPIDs are relative measurement devices, convoluting the response variation due to radiation beam and per pixel characteristics (sensitivity, gain). Thus, the raw EPID images cannot be used to assess radiation beam characteristics. To differentiate between contributions due to radiation beam and per pixel characteristics complex calibration procedures are required. Also the pixel characteristics may vary over time, requiring frequent recalibration.

Currently existing EPID calibration processes try to correlate the measurement of an absolute external measurement device, for example a water phantom, with the EPID image, thereby isolating the contributions of beam and pixels. However, EPIDs are not dosimeters, as the interactions of photons leading to an EPID image is different than the interactions in water or tissue that lead to a radiation dose. Thus, the raw EPID image is not a dose image, and the EPID response deviates from what would be expected based on water-based dose measurements. As such, direct correlation is not possible.

Thus, the ease of using EPIDs makes them attractive for quality assurance (QA) applications, but the images must be corrected for non-linear behavior of the electronics and inhomogeneous pixel sensitivities. Further, in order to use an EPID for measuring energy change, beam alignment, and beam tilt relative to the collimator rotation axis, elaborate calibration procedures need to be implemented to calibrate the EPID's response to the measured values.

There is, thus, a need for an alternative approach to the extensive calibrations procedures currently applied that is independent from external dosimeters and from simulations, and a need for methods, systems, and devices by which EPIDs can be used as measurement devices for beam characteristics as well as for beam alignment without having to implement elaborate calibration procedures.

Further, since many of the modern radiation treatment devices, such as medical LINACS, are equipped with electronic portal imaging devices (EPIDs), there is a need for being able to use the EPIDs as beam alignment measuring devices without extensive calibration protocols in place, in order to be able to perform automatic calibration, tuning, and verification of the radiation treatment systems and devices. Since currently available radiation therapy machine tuning, calibration, and verification protocols are slow, inaccurate, require external hardware, and/or rely on subjective human decisions, employing EPIDs without complex calibration procedures, as disclosed throughout the specification, reduces overall costs, processing, and analysis time, as well as remove operator dependency.

SUMMARY

An object of the present disclosure is to provide a system and method for using an electronic portal imaging device (EPID) as a radiation beam characteristics measuring device as well as beam alignment measuring device without the need for extensive EPID calibration.

Another object of the present disclosure is to provide a system and method for measuring the number of converted high-energy photons using an EPID without needing extensive EPID calibration.

Another object of the present disclosure is to provide a system and method for measuring photon flux and/or fluence using an EPID without needing extensive calibration of the EPID.

Another object of the present disclosure is to provide imaging-based methods for verification of radiation treatment using an electronic portal imaging device (EPID) as a beam characteristics measuring device and beam alignment measuring device without the need for extensive EPID calibration.

Another object of the present disclosure is to provide systems and methods for using an EPID device as a measuring device for determining changes in the radiation beam energy, symmetry, and flatness without the need for complex EPID calibration.

Another object of the present disclosure is to provide a system and method for measuring radiation beam tilt using an EPID.

Another object of the present invention is to provide imaging-based methods for automatic calibration, tuning, and verification of radiation treatment devices and systems. Since many of the modern radiation treatment devices, such as medical LINACS, are equipped with an electronic portal imaging device (EPID), the present invention provides methods for using the EPID to perform the automatic calibration, tuning, and verification of the radiation treatment systems and devices, and therefore, reduce overall costs, processing, and analysis time, as well as remove operator dependency.

Another object of the present invention is to provide specific procedures and image analysis algorithms for the automatic tuning, calibration, and verification protocols.

The present disclosure provides image-based quality assurance protocols to verify that parameters and characteristics of a radiation treatment device are within predetermined specifications using an EPID as a beam measuring and beam alignment device without having to implement complex calibration procedures.

The present disclosure also provides systems and methods for determining radiation beam characteristics using an imaging device without calibrating the imaging device response, the method comprising: acquiring one or more images using the imaging device, determining one or more parameters from the one or more images, and determining one or more characteristics of the radiation beam from the determined one or more parameters. In embodiments, the one or more characteristics includes number of converted high-energy photons, photon flux and/or fluence, radiation beam energy change, radiation beam tilt relative to a collimator axis of rotation, radiation beam symmetry, radiation beam flatness, and radiation beam center change.

The present disclosure also provides radiation treatment systems, comprising: a radiation source configured to emit a radiation beam, an imaging device configured to acquire one or more images, and a processing device configured to execute processor-executable process steps for determining radiation beam characteristics without implementing an imaging device response calibration protocol.

In embodiments, the process steps comprise: acquiring one or more images using the imaging device, determining one or more parameters from the one or more images, and determining one or more characteristics of the radiation beam from the determined one or more parameters. In embodiments, the one or more characteristics includes number of converted high-energy photons, photon flux and/or fluence, radiation beam energy change, radiation beam tilt relative to a collimator axis of rotation, radiation beam symmetry, radiation beam flatness, and radiation beam center change.

In embodiments, the imaging device is an electronic portal dose imaging device (EPID).

The present disclosure also provides for systems and methods for calibrating the radiation treatment system based on the determined one or more radiation beam characteristics. The calibrating can include calibrating control elements of the radiation treatment system, the control elements controlling the characteristics of the radiation beam. The control elements can include one or more of beam collimator devices, beam angle steering coils, beam position steering coils, shunt current sources, beam flattening filters, beam scattering filters, dosimeters, gantry positioning devices, light sources, beam sources, and gun-cathode heating controls.

The present disclosure also provides using an EPID as a measuring device for capturing various characteristics and parameters of a radiation treatment device from images obtained using the EPID, analyzing the various characteristics and parameters from the EPID images, and using the information obtained from the images to modify the performance of the radiation therapy system to achieve the desired tuning and calibration of the system.

The present disclosure also provides systems, devices, and methods for fast and less error prone tuning, calibration, and verification of radiation therapy systems based on images obtained using electronic portal imaging devices, without the implementation of an EPID response calibration procedure.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features.

DETAILED DESCRIPTION

Figure 1:
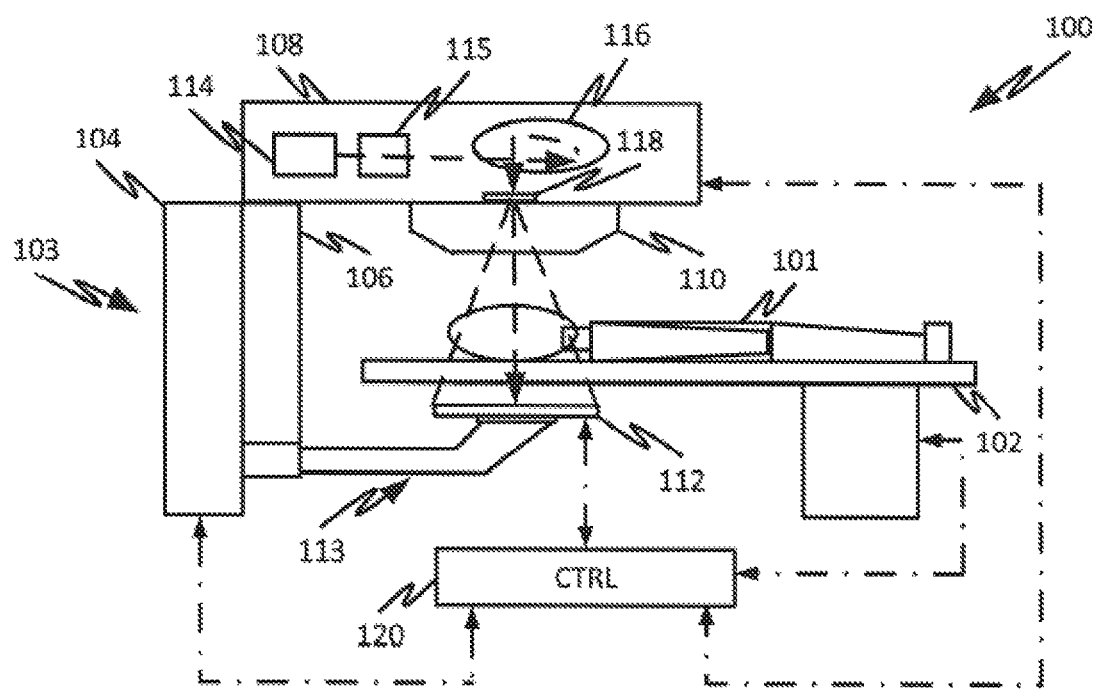
FIG. 1 illustrates a radiation treatment system according to one or more embodiments of the disclosed subject matter.

Patients undergoing radiation therapy are typically placed on the treatment platform of a radiation treatment gantry. The radiation beam irradiates a region of interest in the patient, such as a diseased issue including a tumor or cancerous growth site. When delivering the radiation, a plurality of radiation beams may be directed to the target area of interest from several positions outside the body. The gantry including a radiation source can be rotated to provide the radiation beams from different positions.

The ability to deliver the correct radiation dose to the target area depends on several factors, including exact dose calibration, accurately determined depth dose and off-axis dose characteristics, and knowledge of the precise patient geometry used during irradiation. The influencer of these various factors depends on the type of radiation treatment device used. For example, using isocentric treatment requires understanding of the exact geometry in which the patient is treated. Therefore, the factors influencing accuracy of radiation beam delivery is dependent on the mechanical precision and movements of the machine itself and of the machine and/or treatment accessories such as wedges, blocks, etc. As a result, a quality assurance protocol needs to be implemented to test the dosimetric characteristics and the mechanical and geometric integrity of the radiation treatment system.

There are numerous parameters, such as, beam alignment, beam symmetry, beam shape, beam energy, and beam flatness, associated with a radiation therapy system that influence the accuracy of the radiation dose delivered to the patient. Because these parameters depend on the accurate alignment and placement of various mechanical elements/pieces of the radiation therapy system, the mechanical elements need to be checked and tuned prior to the radiation treatment device being installed and/or used in the radiation treatment facility. Because the mechanical elements affecting these parameters tend to move, the parameters need to be regularly checked and, if a shift is observed from their nominal preset values, the mechanical elements need to be adjusted and retuned during installment, and verified during regular preventive maintenance inspection.

EPIDs have been used for evaluating parameters of the radiation therapy system for some time. Generally, images obtained using an EPID are compared with previously obtained images, and the discrepancies between the images are associated with the parameters of the system. The ease of using EPIDs make them attractive for dosimetry applications, but the images must be corrected for non-linear behavior of the electronics, inhomogeneous pixel sensitivities, scattering in the detector, and the EPID panel's complex energy response.

EPIDs have been used as relative dose measurement devices and as absolute dose measuring devices. The relative dose measurements have the disadvantage of requiring an external reference measurement of some sort, and the corresponding calibration schemes are often tedious. The absolute dose measurements on the other hand have the disadvantage of requiring complex and time-consuming calibration techniques to correct for non-linearity of the EPID response. These calibration techniques also require accurate motion control of the EPID.

In either case, before an EPID can be used to detect dose, and thus number of detected X-ray photons per pixel, the EPID pixel response needs to be corrected for the inherent differences in response or gain of the individual pixels in the imaging matrix of the EPID. Measuring pixel sensitivity variation, however involves a complex process.

In the present embodiments, systems, methods, and algorithms are described by which an EPID can be used to measure the number of detected (converted) X-ray photons, photon fluence, and photon flux, independently of the pixel gains, and thus without extensive calibration of the EPID. This is done by measuring pixel noise across a series of images, and determining the number of detected X-ray photons per pixel based on the measured mean pixel value and the calculated standard deviation for every pixel i in a series of images. In alternative embodiments, instead of measuring the pixel noise using a series of images, the local (spatial) noise within an image is measured and used, as described in detail throughout the disclosure.

In the present disclosure, systems and methods are described for using the EPID as a radiation characteristics and parameters measuring device, without having to implement elaborate calibration procedures. For example, the radiation beam tilt can be determined using an EPID without having to calibrate the EPID for pixel sensitivity variations, because the tilt determination method is independent of the pixel gain. The method comprises determining the intersection of the beam axis with the imager by calculating the ratio of the pixel values of pixels i at two energies $E_1$ and $E_2$. The ratio depicts a circular beam profile centered at the intersection of the beam axis with the imager, and is independent of the imager pixel gain. When the beam is tilted, a non-zero angle $\alpha$ is formed between the beam axis and the collimator rotation axis. This results in the shift of the center of the beam shape as well as a slight distortion of the shape, making it slightly elliptical.

The present invention provides systems and methods for evaluating a plurality of parameters of the radiation therapy system using an electronic portal imaging device (EPID). The present invention also provides systems and methods for verifying the parameters of the radiation therapy system using an electronic portal imaging device (EPID) without needing extensive calibration.

The present invention provides systems and methods for using an EPID as a measurement device for beam alignment, which outperforms the accuracy of the currently used gold standard (i.e., water phantom) by an order of magnitude.

The present invention also provides systems and methods for using an EPID as a measuring device for evaluation of radiation beam energy changes, beam flatness and beam symmetry changes without the need for complex calibration procedures. In embodiments, radiation beam energy changes, beam flatness, and beam symmetry can be determined using an EPID without having to calibrate the EPID for pixel sensitivity variations, and thus, independently of the pixel gain, as described in detail throughout the disclosure. Using the EPID as described offsets any variations in the pixel response of the EPID, and therefore, the EPID can be used without having to calibrate it for such variations. The present disclosure also provides using an EPID as a measuring device for capturing various characteristics and parameters of a radiation treatment device from images obtained using the EPID, analyzing the various characteristics and parameters from the EPID images, and using the information obtained from the images to modify the performance of the radiation therapy system to achieve the desired tuning and calibration of the system.

An exemplary radiation therapy treatment system which uses an EPID as a measuring device is illustrated in FIG. 1. The treatment system 100 is configured to deliver radiation treatment to a patient 101. The treatment system 100 can be configured for dual-mode stereotactic or radiation therapy application, namely, the system 100 can be configured to provide photon-based or electron-beam based radiation treatment to a patient 101 positioned on a treatment couch 102. The gantry 106 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the treatment beam source at various rotational and/or axial positions relative to the patient 101 may also be used. The system 100 also includes a treatment couch 102 which can be positioned adjacent to the gantry 106 to place the patient 101 and the target volume within the range of operation of the treatment beam during radiation treatment. The treatment couch 102 may be connected to the rotatable gantry 106 via a communications network and is capable of translating in multiple planes to reposition the patient 101 and the target volume. The treatment couch 102 can have three or more degrees of freedom.

The radiation therapy system 100 includes a radiation treatment device 103, such as, but not limited to, a dual-mode (photon and electron-beam) medical LINAC device configured for stereotactic or radiation therapy application. The radiotherapy device 103 includes a base or support structure 104 supporting the gantry 106. The gantry 106 is supporting an electron beam accelerator module 108 which can include an electron gun 114 for generating electron beams and an accelerator waveguide 115 for accelerating the electron beams from the electron gun 114 toward an X-ray target 118 (when the radiation treatment device 103 operates in a photon mode) or toward an electron beam exit window (not shown), when the radiation treatment device 103 operates in an electron-beam mode. The electron beam exit window allows the electron beam to exit the electron beam accelerator module 108 and enter a LINAC treatment head 110. The accelerating waveguide 115 can be mounted parallel to the gantry rotation axis, and thus the accelerated electron beam must be bent for it to strike the X-ray target 118 (when device 103 operates in the photon mode) or the exit window (when device 103 operates in an electron-beam mode). The accelerating waveguide 115 can also be mounted parallel to the collimator rotation axis. An electron beam transport system 116 can include bending magnets, steering coils, trim coils, and a gun cathode heating circuit can be used for bending and steering the accelerated electron beams toward the X-ray target 118 or the exit window. The electron beam transport system 116 can bend an electron beam at 90 degrees, 270 degrees (achromatic bending) and at 112.5 degrees (slalom bending) by adjusting the shunt current applied to the bend magnet from a current source (not shown). When the electron pencil beam hits the X-ray target 118, it generates the clinical photon beams (X-rays). The location at which the X-rays are generated is referred to as the radiation beam spot or radiation source.

In operation, electrons originating in the electron gun 114 are accelerated in the accelerating waveguide 115 to the desired kinetic energy and then brought, in the form of a pencil electron beam, through the beam accelerator module 108 into the LINAC treatment head 110, where the clinical photons, such as X-rays, (when the device 103 operates in the photon mode) or the electron beams (when device 103 operates in the electron-beam mode) are produced. The LINAC treatment head 110 contains several components that influence the production, shaping, localizing, and monitoring of the clinical photon beams, as shown in detail in FIG. 3, or the clinical electron beams, as shown in detail in FIG. 4.

The radiation treatment device 103 also includes a holding structure 113, which could be a retractable robotic, servo controlled arm, holding an imager 112 for acquiring digital images. The imager 112 is an electronic portal imaging device (EPID). The holding structure 113 is used to position the EPID 112 and allow movement of the EPID 112 vertically (along the Z-axis), laterally (along the X-axis), and longitudinally (along the Y-axis). The EPID 112 can be mounted onto the rotating gantry 106 in opposition to the radiation source, such that the clinical radiation beam, namely the photon or the electron beam, from the LINAC head 110 is received by the EPID 112. The EPID 112 can have a detector surface corresponding to the cross-sectional area of the clinical radiation beam.

In operation, the EPID 112 produces electronic signals providing measurements of the dose of the radiation received at the detector surface at regularly spaced positions over the detector surface. The signals from the EPID 112 are transmitted to a computer processor of the controller 120 where it is converted into a matrix of digital values, the values indicating the dose of radiation at each point of the imager surface. A projection image derived from the matrix of digital values can be displayed on a display of the controller 120.

The controller 120 manages images and related information, such as transforming the data stream from the EPID 112 into a standard video format, the synchronization of the imager 112 and the LINAC treatment head 110 based on the different types of images acquired with the EPID 112, as well as image transfer, frame processing, and image calibration. The controller 120 can also store and display the final dose image as well as instructions for taking corrective actions. Controller 120 can include a computer with typical hardware, such as a processor, and an operating system for running various software programs and/or communication applications. The computer can include software programs that operate to communicate with the radiation treatment device 103, which software programs are operable to receive data from external software programs and hardware. The computer can also include any suitable input/output devices adapted to be accessed by medical personnel, as well as input/output (I/O) interfaces, storage devices, memory, keyboard, mouse, monitor, printers, scanner, etc. The computer can also be networked with other computers and radiation therapy systems. Both the radiation therapy device 103 and the controller 120 can communicate with a network as well as a database and servers. The controller 120 can also be configured to transfer medical image related data between different pieces of medical equipment.

The system 100 also includes a plurality of modules containing programmed instructions (e.g., as part of controller 120, or as separate modules within system 100, or integrated into other components of system 100), which instructions cause system 100 to perform different tuning, calibration, and verification functions related to the radiation treatment device 103, as discussed herein, when executed. The modules can be written in C or C++ programming languages, for example. Computer program code for carrying out operations as described herein may also be written in other programming languages.

Figure 2A:
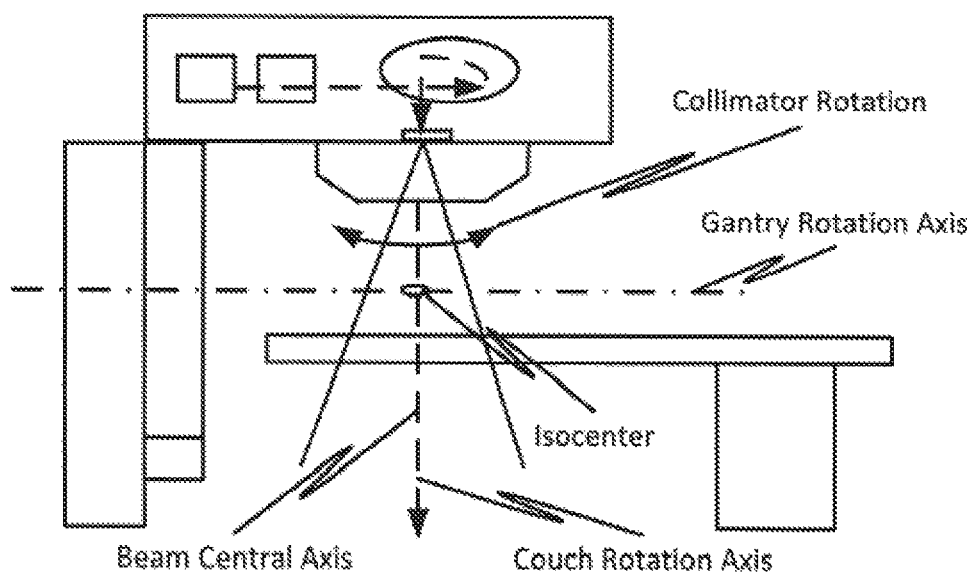
FIGS. 2A and 2B illustrate the rotation axes and coordinate frame orientation of the radiation treatment device of FIG. 1.
Figure 2B:
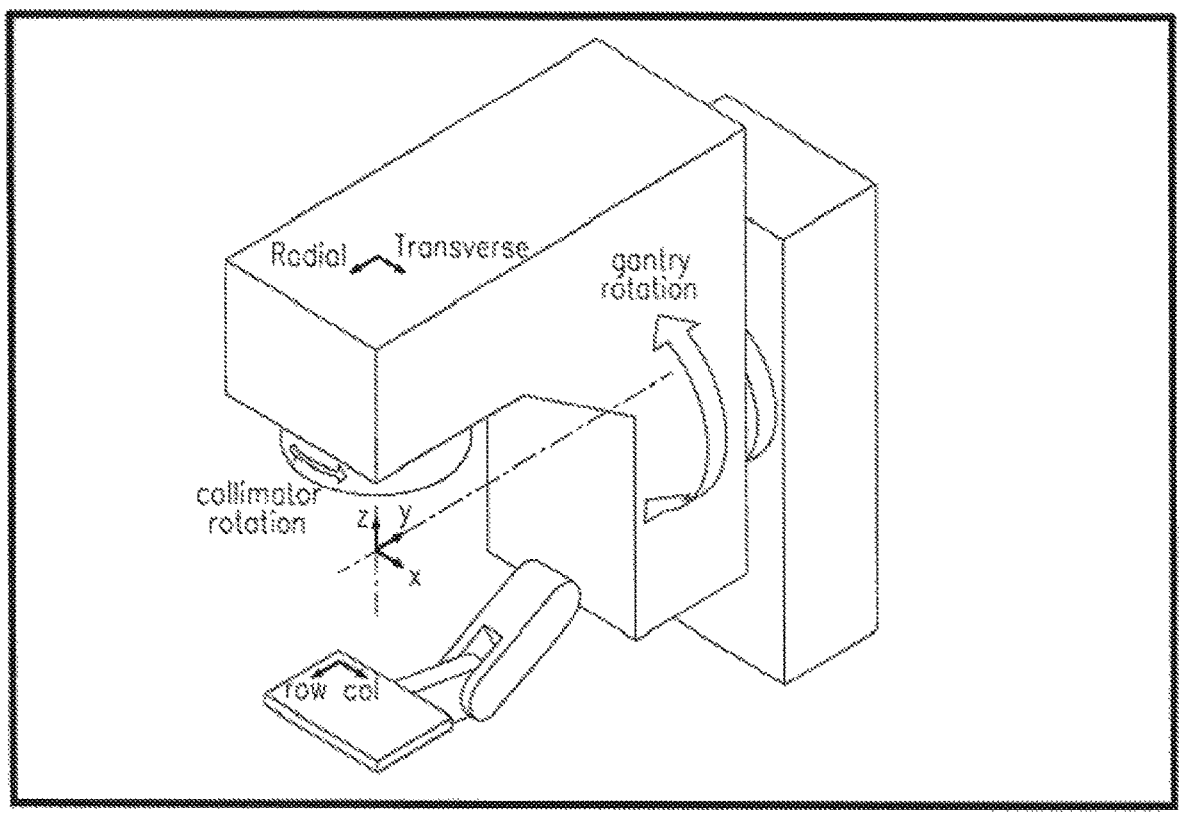

The system 100 including the EPID 112 integrated with the radiation treatment device 103 allows all image guidance activities, such as, image acquisition, image registration, image interpretation, EPID image calibration, and machine calibration to occur automatically and remotely. System 100 also allows capture of all data needed for the image acquisition, evaluation, and calibration (i.e., data relating to gantry, collimator jaws, MLC, light field source, EPID, EPID arm structure, phantom, filters, scattering foils, X-ray target, dose measuring device, beam steering coils, type of image to be acquired, EPID image calibration, etc.). Image interpretation to determine and evaluate different parameters and characteristics of the radiation treatment device 103 can be performed using different algorithms. The determination of adjustments needed to be made in the control element outputs based on the evaluated parameters and characteristics may also be determined using different algorithms. Once the required adjustments are determined, the necessary tuning and/or calibration and/or verification protocols are automatically sent to the radiation treatment device 103 and the control elements are automatically or manually adjusted until their outputs fall within accepted ranges. FIGS. 2A and 2B illustrate the radiation beam central axis, the gantry rotation axis, the treatment couch rotation axis, the collimator rotation axis, and the isocenter of system 100.

Figure 3:
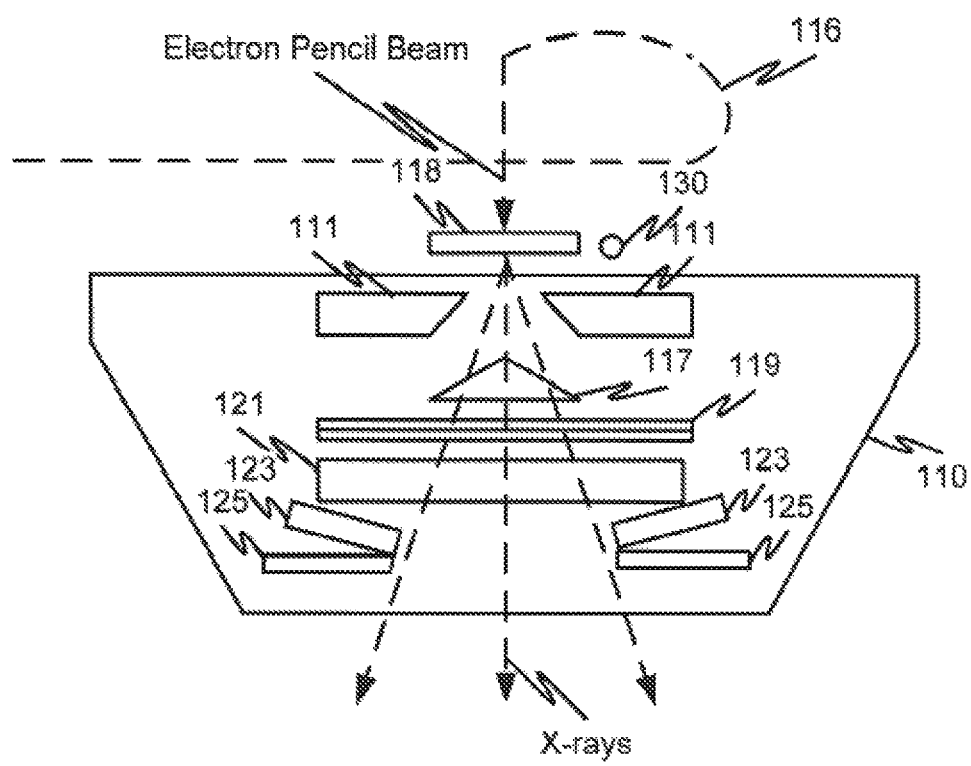
FIG. 3 illustrates a linac treatment head used in a radiation treatment system operating in a photon generation mode.

FIG. 3 illustrates a LINAC treatment head 110 when the device 103 operates in a photon mode. The LINAC treatment head 110 can include one or more retractable X-ray targets 118 where clinical photon beams, such as X-rays, are produced, none, one or more flattening filters (FF) 117, which can be mounted on a rotating carousel or sliding drawer for ease of mechanical positioning of the filters 117 into the X-ray beam, dual transmission ionization chambers 119, a collimating device (i.e., collimator) including primary collimators 111, adjustable secondary collimators with two upper jaws 121 and two independent lower jaws 123, multileaf collimators (MLC) 125, and a field defining light source 130.

Primary collimators 111 define a maximum circular radiation field, which is then further truncated with the adjustable secondary collimators (121, 123) to produce rectangular and square fields at the LINAC isocenter. The primary collimator 111 defines the largest available circular field size and is a conical opening that can be machined into a tungsten shielding block, for example, with the sides of the conical opening projecting on to edges of the X-ray target 118 on one end of the block, and on to the flattening filters 117 on the other end. The thickness of the shielding block is usually designed to attenuate the average primary X-ray beam intensity to less than 0.1% of the initial value. Any other applicable material besides tungsten can also be used.

The secondary beam defining collimators include four blocks, two forming the upper jaws 121 and two forming the lower jaws 123. They can provide rectangular and square fields at the LINAC isocenter, with sides of the order of few millimeters up to 40 cm. Alternatively, the jaws could be independent asymmetric jaws to provide asymmetric fields, such as one half or three quarter blocked fields in which one or two beam edges are coincident with the beam central axis. The optional multileaf collimators (MLC) 125 can be made of 120 movable leaves with 0.5 cm and/or 1.0 cm leaf width, for example. For each beam direction, an optimized intensity profile is realized by sequential delivery of various subfields with optimized shapes and weights. When using MLCs, from one subfield to the next, the leaves may move with the radiation beam on (i.e., dynamic multi-leaf collimation (DMLC)) or with the radiation beam off (i.e., segmented multi-leaf collimation (SMLC)). Such an MLC system can cover fields up to 40×40 $cm^2$, for example, and can require 120 individually computer controlled motors and control circuits. Miniature versions of the MLC can also be used. For example, miniature MLCs that project 1.5-6 mm leaf widths and up to 10×10 $cm^2$ fields at the LINAC isocenter, could also be used.

The ionization chamber 119 could be a dual transmission ionization chamber used for monitoring the photon radiation beam output as well as the radial and transverse beam flatness. The ionization chamber 119 acts as an internal dosimeter, and can be permanently imbedded into the LINAC treatment head 110 to continuously monitor the radiation beam output. The ionization chamber 119 could also be sealed to make its response independent of ambient temperature and pressure. The ionization chamber 119 can include a primary and a secondary ionization chamber with the primary chamber measuring monitor units (MUs). Typically, the sensitivity of the chamber electrometry circuitry is adjusted in such a way that 1 MU corresponds to a dose of 1 cGy delivered in a water of phantom at the depth of dose maximum on the central beam axis when irradiated with a 10×10 $cm^2$ field at a source to surface distance (SSD) of 100 cm. Once the operator preset number of MUs has been reached, the primary ionization chamber circuitry shuts the radiation treatment device 103 down and terminates the dose delivery to the patient 101. Before a new irradiation is initiated, the MU display is reset to zero.

In addition to monitoring the primary dose in MUs, the ionization chamber 119 can also monitor other operating parameters such as the beam energy, flatness and symmetry. Measurements of all of these additional parameters requires that the ionization chamber electrodes of the primary and secondary chambers be divided into several sectors, with the resulting signals used in automatic feedback circuits to steer the electron beam through the accelerating waveguide 115 and the beam transport system 116 and onto the X-ray target 118 or scattering foils 127, thereby ensuring consistent beam flatness and symmetry.

The LINAC treatment head 110 can also include a field defining light source 130 to provide a convenient visual method for correctly positioning the patient 101 for treatment using reference marks. The light source 130 may be mounted inside the collimator and can be positioned at the location of the X-ray target 118 by a rotating carousel or a sliding drawer assembly, or it may be positioned to one side of the collimator axis of rotation with the light reflected by a mirror. In clinical operations, the light field illuminates an area that coincides with the radiation treatment field on the patient's skin and the alignment of the light field with the skin marks on the patient is used as the final confirmation that the patient 101 is correctly positioned with respect to the radiation beam. It is therefore important that the light field agrees (is congruent) with the radiation field.

Figure 4:
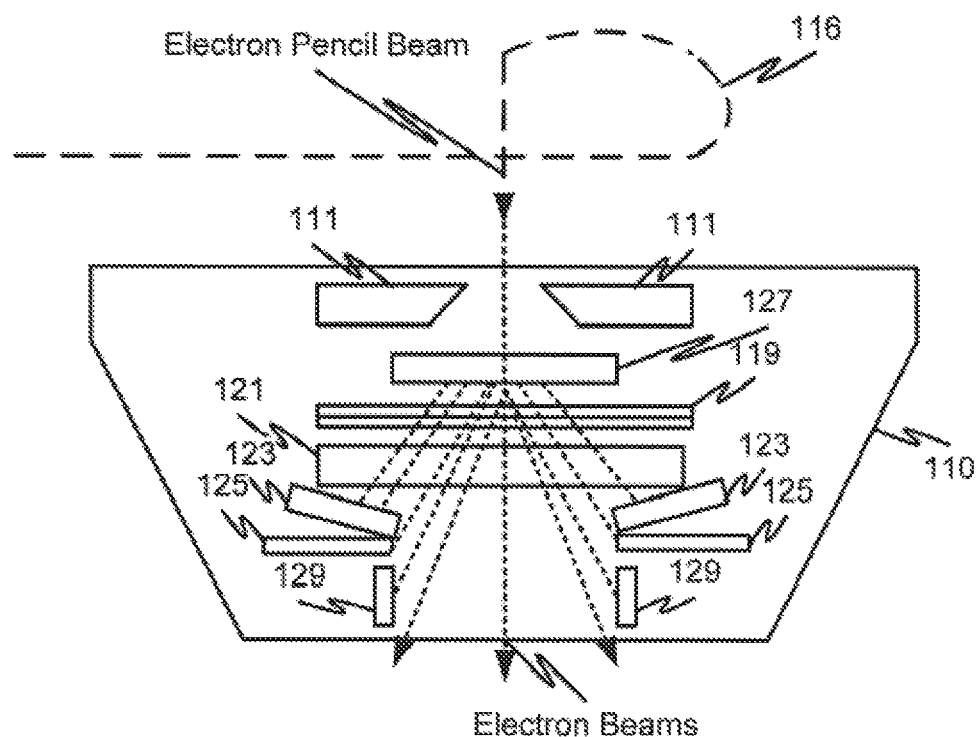
FIG. 4 illustrates a linac treatment head used in a radiation treatment system operating in an electron-beam generation mode.

When the radiation treatment device 103 operates in an electron-beam mode, the LINAC treatment head 110 does not need the X-ray target 118 and the flattening filters 117. FIG. 4 illustrates a LINAC treatment head 110 when the radiation treatment device 103 operates in the electron-beam mode. To activate an electron-beam mode, both the X-ray target 118 and the flattening filters 117 used in the photon mode are removed from the electron pencil beam path. The electron pencil beam exits the beam accelerator module 108 through a thin window (not shown) usually made of beryllium, which minimizes the pencil beam scattering and bremsstrahlung production. To produce clinical electron beams from the electron pencil beams, thin scattering foils 127 of a high atomic number (copper or lead, for example) are positioned into the electron pencil beam at the level of the flattening filters 117 in the X-ray mode. In addition to the primary 111 and secondary collimators 121, 123, the clinical electron beams also rely on electron beam applicators (cones) 129 for beam collimation. The rest of the collimation and beam shaping elements are the same as in the photon-beam mode.

Figure 5A:
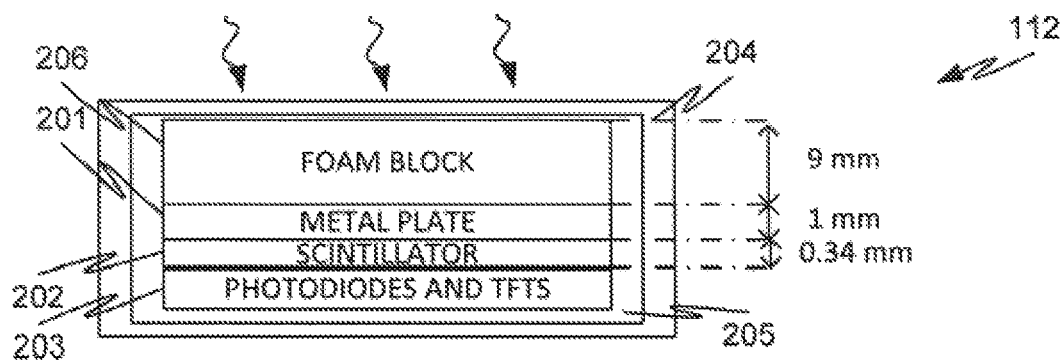
FIGS. 5A-5C illustrate an exemplary imaging device used in the radiation treatment device of FIG. 1.
Figure 5B:
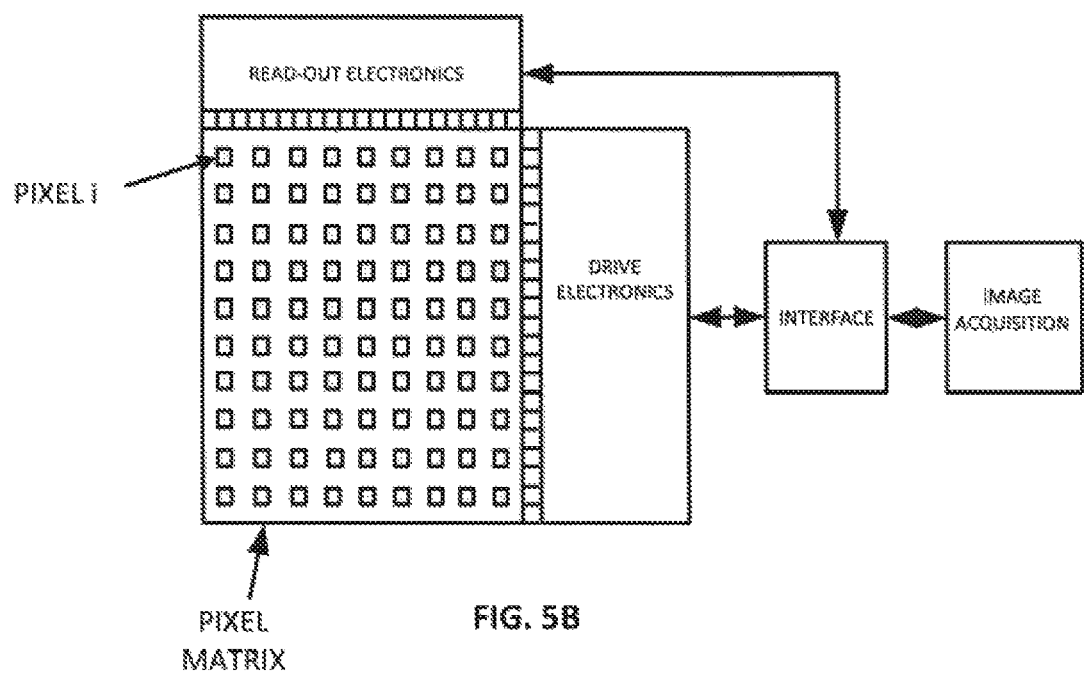
Figure 5C:
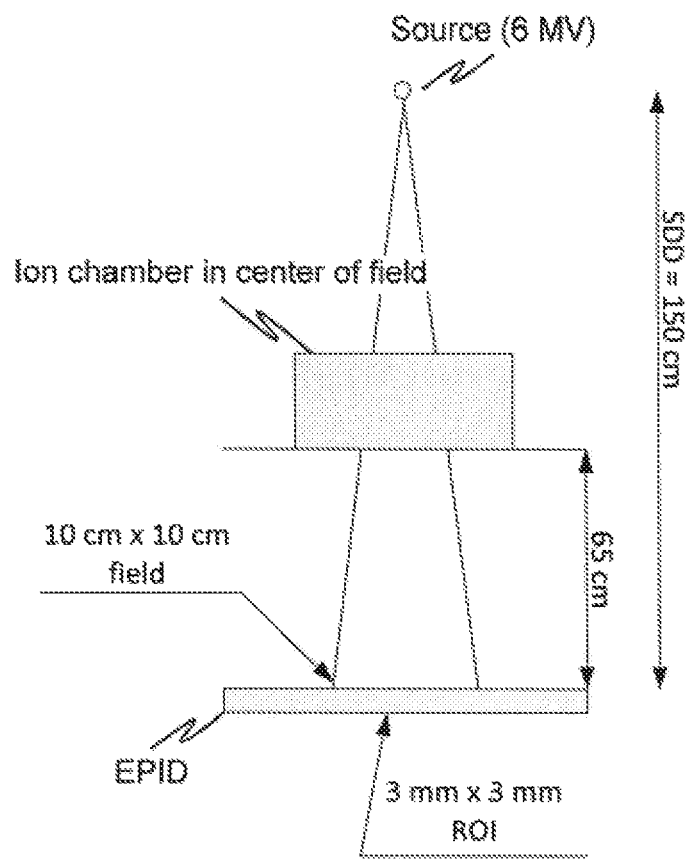

FIGS. 5A-5C illustrate an exemplary EPID 112 used to generate EPID images. The EPID 112 could be an amorphous silicon type detector panel including a 1 mm copper plate 201 to provide build-up and absorb scattered radiation, and a scintillating phosphor screen 202 made of terbium doped gadolinium oxysulphide to convert the incident radiation to optical photons. The scintillating screen 202 can have a thickness of 0.34 mm, for example. The EPID 112 can also include a pixel matrix 203 created from an array of 1024× 768 or 1280×1280 pixels i, where each pixel i is made up of a photodiode to integrate the incoming light and a thin film transistor (TFT) to act as a three-terminal switch for readout. The EPID 112 can also include electronics to read out the charge from the transistor and translate it into an image data.

The imager 112 can also be enclosed in a protective plastic cover 204 with an air gap 205 between the protective cover and the copper plate 201. Alternatively, layers of foam 206 and paper can be included between the protective cover and the copper plate. The protective cover can be about 3 cm above the effective point of measurement. The EPID can be positioned at source to EPID distances (SDD) from 95 cm to 180 cm. It can also have an active imaging area of 40×30 cm$^2$ or 43×43 cm$^2$ (at an SDD of 150 cm), for example. The maximum frame acquisition rate can be 15 frames/second, the permitted energy range can be between 4-25 MeV, and the permitted dose rates can be between 50-600 MU/min, for example. However, any other applicable EPIDs can be used, as the measuring device 112.

EPID as X-Ray Photon Counting Device

Converting EPID images to dose generally includes generating a correction matrix by which the EPID pixels need to be corrected. The correction matrix takes into account corrections that need to be made for inherent differences in response or gain of the individual pixels in the imaging matrix of the EPID. Measuring pixel sensitivity variations, however, is a complex process. Thus, generating such a correction matrix generally involves a complex calibration process.

In the present embodiments, systems, methods, and algorithms are described by which an EPID can be used to measure the number of detected (converted) X-ray photons without the need for complex calibration procedures. The methods disclosed allow for using an EPID to measure the number of photons per pixel without having to calibrate the EPID for pixel gain variations, because the number of detected X-ray photons per pixel are determined independent of the gain of the pixel. In the present embodiments, systems, methods, and algorithms are also described by which an EPID is used to measure the photon flux and/or photon fluence without the implementation of complex calibration procedures.

Using an EPID as a photon measuring device in this fashion is based on the observation that in an EPID, the image noise is dominated by X-ray photon noise. Note that in a scintillator-based EPID, X-ray detection is based on an indirect conversion, meaning that the X-rays are converted into visible light (subsequently also referred to as optical photons), which is then converted into electric charges. One single converted X-ray photon generates a large number of optical photons. In contrast to this, an EPID may also be based on direct-conversion detectors, in which case the X-ray photons are directly converted into electric charge. In any case, the pixel value (i.e., signal measured for a pixel i in the EPID) is linearly related to the number of X-ray photons $N_i$ detected for each pixel i.

The relationship between the pixel value and the number of detected X-ray photons is:

$$\text{value}_{pixel} = \text{number}_{photons} * \text{gain} \quad (1)$$

$$\text{or } p_i = N_i * g_i \quad (2)$$

where the gain $g_i$ (in units of pixel values per photon) is a measure of how the digitally recorded signal relates to the actual photons detected, and $\text{number}_{photons}$ refers to the number of detected X-ray photons.

The mean (i.e., the average) of the pixel value $m_{pi}$ over a series of images is related to the mean (i.e., the average) of the number of photons $m_{Ni}$ by:

$$\text{mean}_{value} = \text{mean}_{photons} * \text{gain} \quad (3)$$

$$\text{or } m_{pi} = m_{Ni} * g_i \quad (4)$$

Similarly, the standard deviation σ (i.e., standard deviation is a measure used to quantify the amount of variation or dispersion of a set of data values) and the variance (i.e., the average of the squared differences from the mean value) in a given pixel i is related to the standard deviation and variance of the photon number by the same proportionality constant $g_i$:

$$\sigma_{pi} = \sigma_{Ni} * g_i \quad (5)$$

$$\sigma_{pi}^2 = \sigma_{Ni}^2 * g_i^2 \quad (6)$$

The actual value of the variance $\sigma_{pi}^2$ of the pixel signal is the result of several noise variance contributions adding up, for instance, the noise of the detected x-ray photons, the noise of the visible (optical) photons, the dark (electronic) noise of the EPID pixel, and the contribution coming from the variation of dose between individual images.

In the particular case of megavoltage (MV) image series, and assuming that an appropriate normalization is used to compensate dose variations between individual images, the Poisson noise of the high-energy X-ray photons is often dominant. In particular, the dark (or electronic) noise of the EPID pixels is usually low enough to allow for a reliable measurement of photon noise, and in scintillator-based EPIDs, the noise of the optical photons can usually be neglected.

Thus, it can be assumed that the noise is dominated by the Poisson noise of the high-energy (i.e. X-ray) photons detected by the EPID. In this case, $\sigma_{pi}$ is given by the square root of the number of X-ray photons, and the variance relates to the mean by:

$$\sigma_{Ni}^2 = m_{Ni} \quad (7)$$

it follows that:

$$m_{Ni} = m_{pi}/g_i \quad (8)$$

$$\sigma_{Ni}^2 = \sigma_{pi}^2/g_i^2 \quad (9)$$

$$\text{and } g_i = \sigma_{pi}^2/m_{pi} \quad (10)$$

$$\text{or } N_i = (m_{pi}/\sigma_{pi})^2 \quad (11)$$

Thus, in an EPID as shown in FIG. 5B, the response of any pixel i in the pixel panel detecting $N_i$ X-ray photons can be described as:

$$p_i = g_i * N_i \quad (12)$$

$$\sigma_i = g_i * \sqrt{N_i(2)} \quad (13)$$

where $p_i$ is the pixel value (i.e., the signal measured by pixel i), $\sigma_i$ is the noise value of the pixel i (i.e., noise at pixel i), and $g_i$ is the gain value of the pixel. By dividing equations (12) and (13), the number of detected X-ray photons per pixel $N_i$ can be obtained from:

$$N_i = (p_i/\sigma_i)^2 \quad (14)$$

As such, by calculating the mean pixel value (corresponding to $p_i$) and the standard deviation (corresponding to $\sigma_i$) for every pixel i in a series of images, the corresponding number of detected X-ray photons per pixel $N_i$ can be calculated independent of the gain $g_i$ of the pixel.

Equation (14) was obtained assuming that the Poisson noise of the X-ray photons is the only contribution to the noise variance $\sigma_{Ni}^2$ in equation (7). However, the contribution of dark noise to the total variance becomes more important for lower photon number (e.g. lower dose per image) and will lead to a systematic underestimation of the X-ray photon number obtained from equation (14). The influence of dark noise can be taken into account by estimating the dark pixel noise variance from a series of dark images (i.e. taken without dose) and subtracting it from the total variance on the left side of equation (7).

Figure 6:
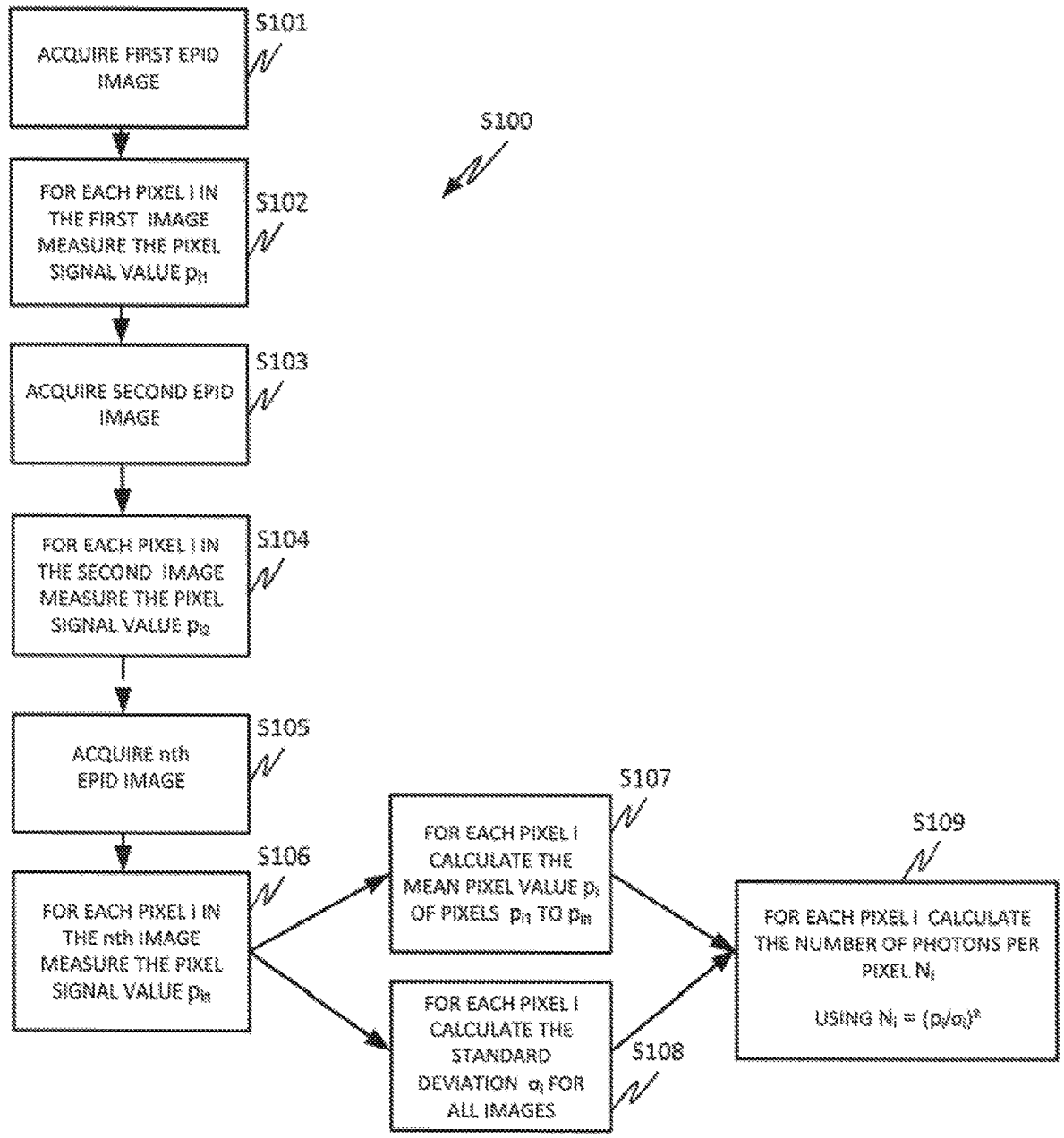
FIG. 6 illustrates an exemplary flow diagram for measuring the number of converted photons using an EPID.

To measure photon flux, process S100 as shown in FIG. 6 can be implemented. In Step S101, a first EPID image is generated. For each pixel i in the first image, the pixel value $p_{i1}$, which represents the signal measured at pixel i is obtained (S102). In step S103, a second EPID image is acquired. As for the first image, for each pixel i in the second image, the pixel value $p_{i2}$ is measured (S104). The process is repeated for n number of images (S105), so that in the $n^{th}$ image, for each pixel i, the pixel value pin, is measured. Then, for each pixel i, the mean value $p_i$ is calculated from the individual pixel values $p_{i1}$, $p_{i2}$, $p_{i3}$, . . . , $p_{in}$ (S107). The mean value $p_i$ can be calculated using:

$$p_i = \frac{pi1 + pi2 + \cdots + pin}{n} \quad (15)$$

In Step S108, for each pixel i, the standard deviation $\sigma_i$ is calculated from the individual pixel values $p_{i1}$, $p_{i2}$, $p_{i3}$, . . . , $p_{in}$.

Alternatively, the pixel noise can also be calculated by averaging the square differences of pixel values of consecutive images and dividing the result by 2, to be less sensitive to systematic long-term drifts.

Then, in step S109, for each pixel i, the number of photons per pixel is calculated using:

$$N_i = \frac{pi}{\sigma i} \quad (16)$$

The underlying assumption in determining photon flux and thus radiation dose this way is that the total number of created photons (the sum of all $N_i$) is constant across the plurality of images. While this is generally not the case, it can be corrected by normalizing the pixel values by the dose per image. However, in order to do that, the dose per image needs to be known more accurately than the pixel values, and thus it needs to have a signal to noise ratio (SNR) above $\sqrt{N}$, which would require an ion chamber accuracy of 0.3% or less. Moreover, for image read-out synchronized to beam pulses, the dose per pulse in most cases is not even known.

In order to remove this issue, in an embodiment using Megavoltage (MV) image series, the mean pixel value within a region of interest (ROI) of the image itself is used for dose normalization. The mean pixel value within an ROI of an image is the average of the pixel values of the pixels that comprise that ROI. For a ROI containing e.g. 100,000 pixels, this may result for instance in a signal to noise ratio (SNR) 100 times larger than for an individual pixel (for fully uncorrelated pixels, the square of the improvement factor would be 100,000). Thus, when the pixel values within the ROI across the series of images are used in the calculations, it effectively replaces the ion chamber value used to normalize the pixel values. If the dose normalization of an image series is based on the mean pixel value of an ROI, the resulting noise variances of the individual pixels in this ROI will be slightly lower than for a dose normalization based on the ion chamber values of each image. The systematic error of dose normalization based on a mean ROI value, however, is by construction small compared to the individual pixel noise to be measured.

Thus, in alternative embodiments, instead of measuring the pixel noise using a series of images, the local (spatial) noise within an image is measured and used. However, this requires the measured beam to be more or less constant within the region of interest (ROI) used to determine the local noise, and the variation between individual pixel gains needs to be compensated by a pixel gain map that is precise enough to reduce the pixel gain variation to a level that is negligible compared to the local noise to be measured.

Figure 7:
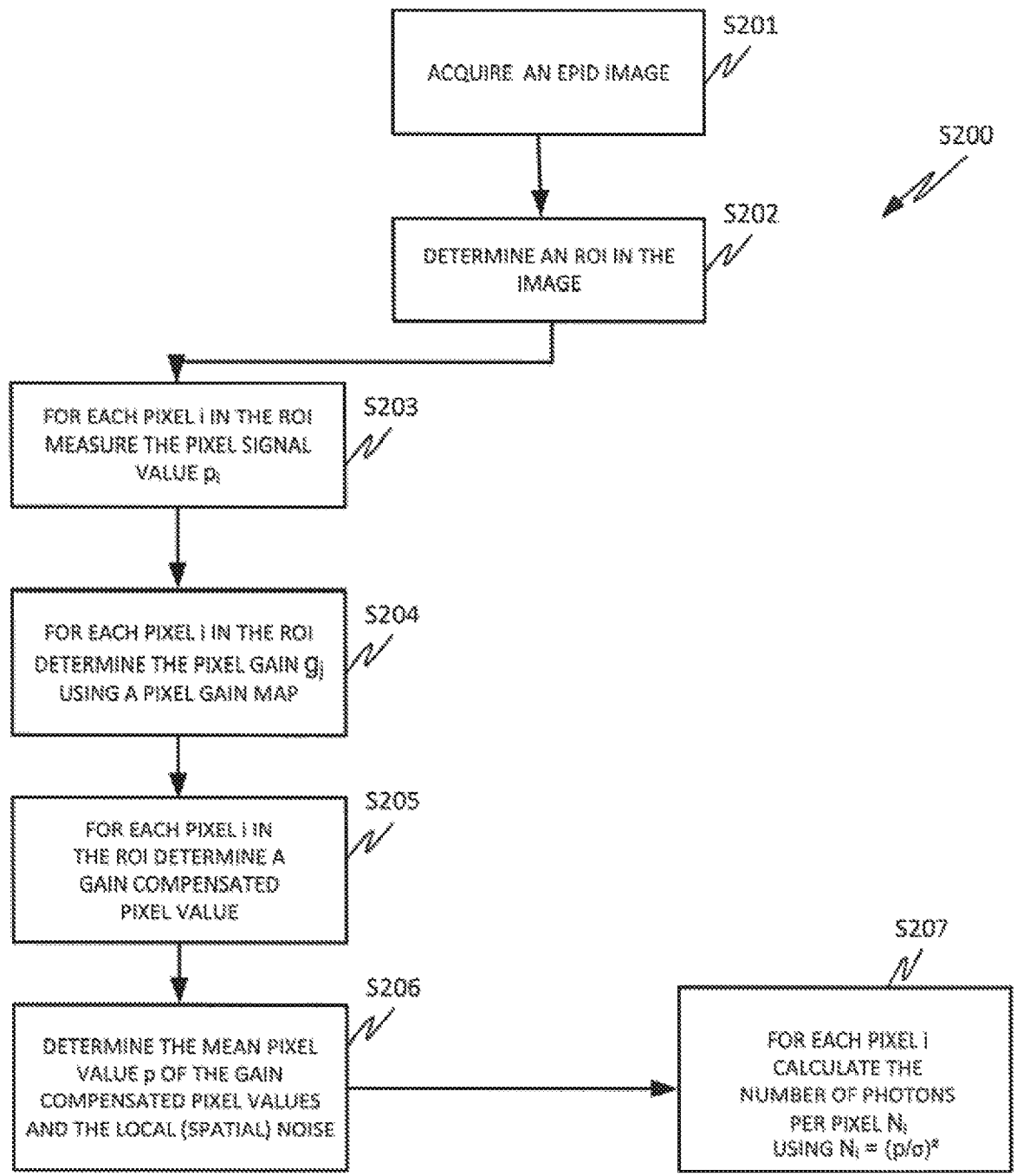
FIG. 7 illustrates another exemplary flow diagram for measuring the number of converted photons using an EPID.

The process S200 for using an EPID as a photon flux measuring device when local noise is measured is shown in FIG. 7, and includes the following steps: In Step S201, a first EPID image is generated. Next, a region of interest (ROI) is determined in the image (S202). For each pixel i in the ROI, the pixel value pi, which represents the signal measured at pixel i is obtained in S203. By applying a previously generated pixel gain map (S204), for each pixel i in the ROI, a pixel gain compensated pixel value is generated (S205) by scaling the pixel value $p_i$ based on the pixel gain $g_i$. The pixel gain map can be generated using any known pixel gain map generation methods.

Then, the mean pixel value p of the gain compensated pixel values is determined in S206. The mean value p is calculated from the individual gain compensated pixel values $p_1$, $p_2$, $p_3$, . . . , $p_n$ using:

$$p = \frac{p1 + p2 + \cdots + pn}{n} \quad (17)$$

In Step S206, the local (spatial) noise value for the pixels in the ROI is also calculated by calculating the standard deviation a of the individual gain compensated pixel values $p_1$, $p_2$, $p_3$, . . . , $p_n$.

Then, in step S207, for each pixel i in the ROI, the number of photons per pixel $N_i$ is calculated using:

$$N_i = \frac{p}{\sigma} \quad (18)$$

In all calculations, it is assumed that the pixel values are dark field offset corrected pixel values.

EPID as Beam Alignment Measuring Device

For the accurate radiation delivery to the patient 101 under the radiation treatment device 103, it is important that the electron pencil beam hits the X-ray target 118 at a perpendicular angle. When the electron pencil beam hits the X-ray target 118 at a perpendicular angle, the radiation beam generated from the X-ray target 118 is symmetric. The symmetry of a radiation beam is considered with regards to the radiation beam center as it is projected from the radiation source 118 past the radiation limiting devices (collimator jaws) to the isoplane.

Figure 8:
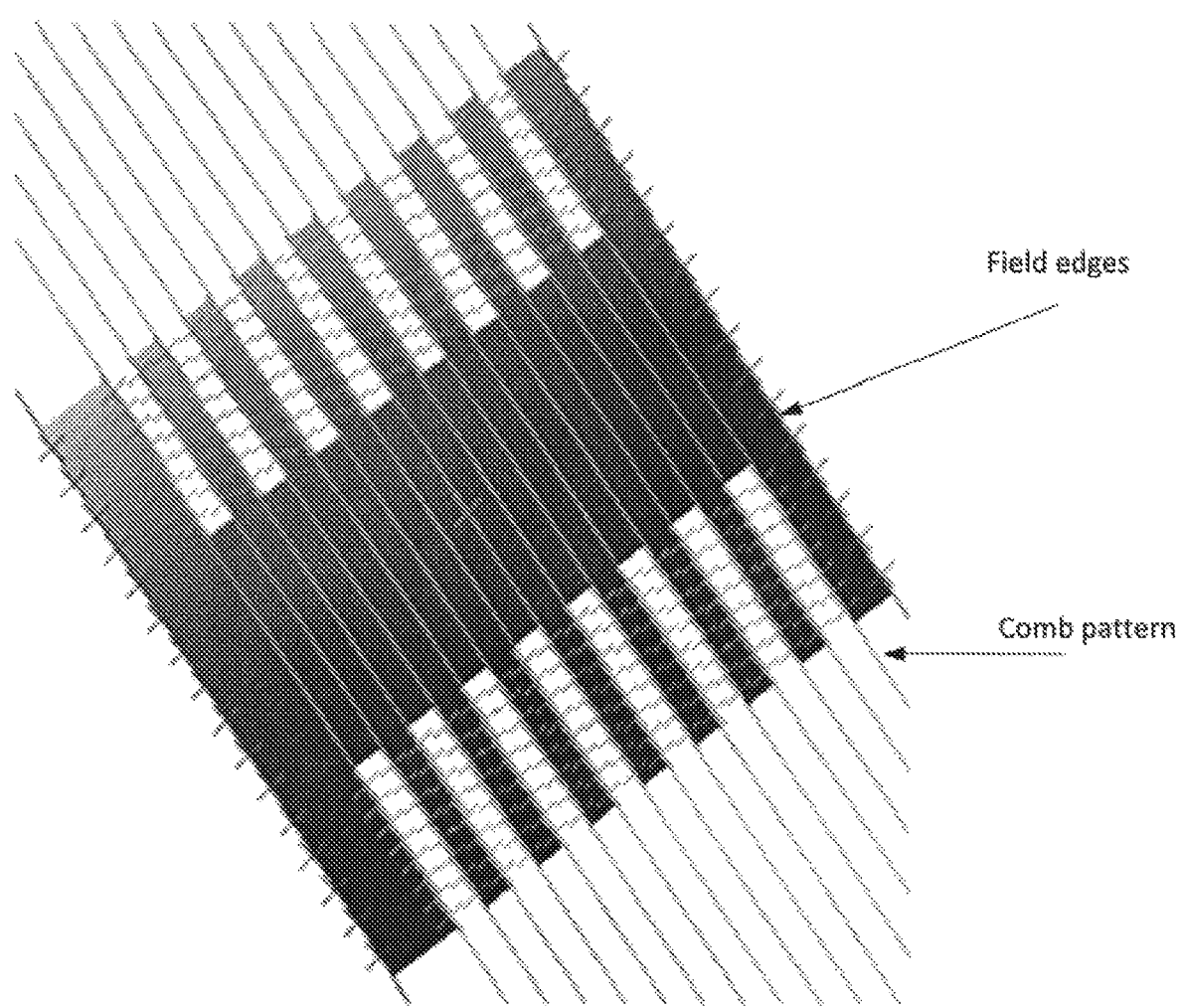
FIG. 8 illustrates field edges and comb patterns formed by a collimator used in the radiation treatment device of FIG. 1.
Figure 9:
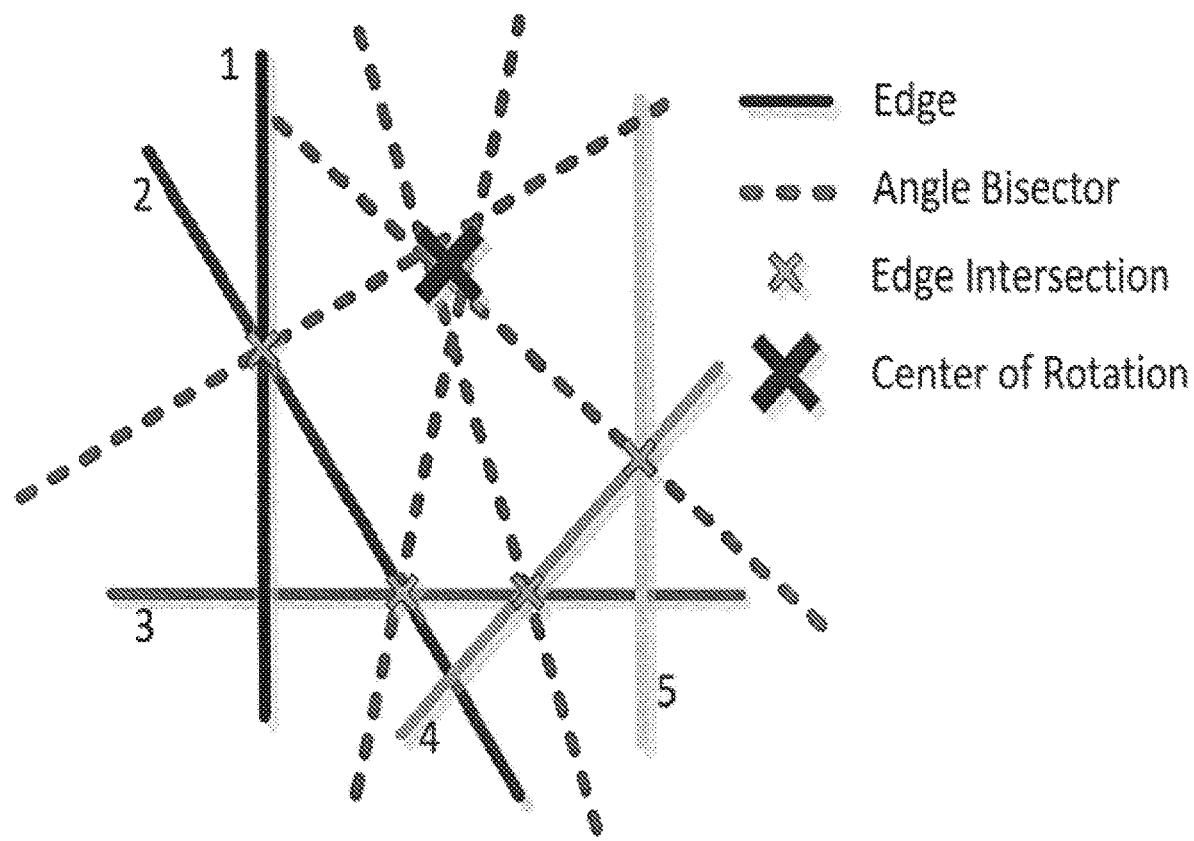
FIG. 9 illustrates an example of how the detected edges at different collimator angles are combined according to an embodiment.

The beam center is defined as the collimation rotation center at a certain height projected from the radiation source onto the image plane. The beam center can be calculated by taking a plurality of images (five, for example) with the collimator MLC rotating, and calculating the beam center from the set of (five) images obtained. Generally, the MLC jaws or leaves at a first height form a comb pattern, and the MLC jaws or leaves at a second, different height are used to shape the left/right field edges as shown in FIG. 8. In order to determine the beam center, the detected edges at different collimator angles are combined as shown in FIG. 9, for example. For each pair of subsequent edges, the angle bisector line is calculated. This results in four angle bisectors. Ideally, this set of lines intersects at the center of rotation. A least squares approach is then applied for finding the point in space with the least distance to all bisection lines. This point in space is the beam center. Any other beam center determination method can be applied. If the radiation source position is on the collimation rotation axis, the beam center is independent of the height of the collimation element used to determine the center. If not, the beam center is determined based on the difference between the source position and the collimation rotation axis.

In the radiation treatment field, the symmetry is considered along the X-axis and the Y-axis, with the Z axis being from the radiation source to the isoplane, and the Y axis increasing from the center toward the gantry stand structure, as shown in FIGS. 2A and 2B. Adjusting the angle of incidence of the electron pencil beam onto the X-ray target 118 can be accomplished by adjusting the angle steering coils in the radial and transverse directions, or with mechanical adjustments of the guide on low energy radiation treatment devices.

Figure 10:
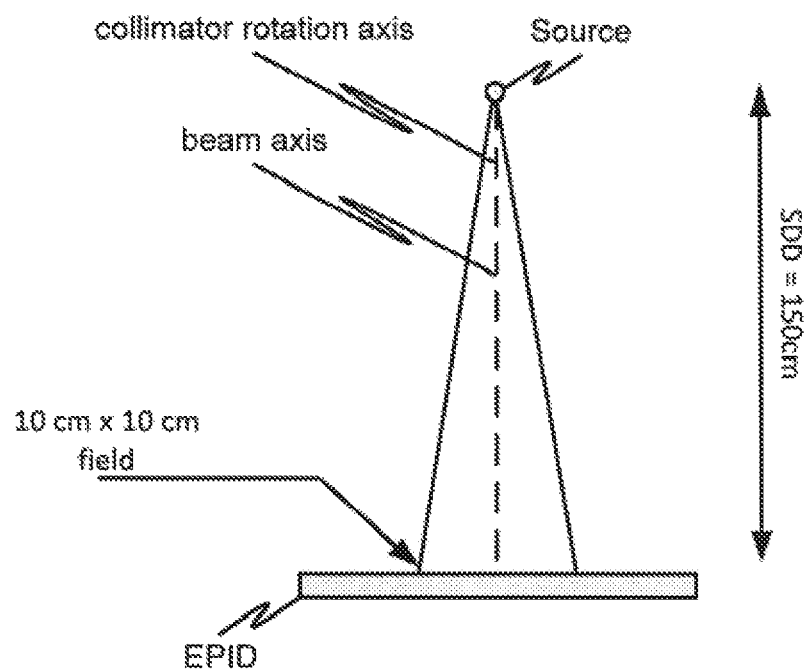
FIG. 10 illustrates a radiation beam axis and collimator rotation axis when radiation source is neither shifted nor tilted.
Figure 11A:
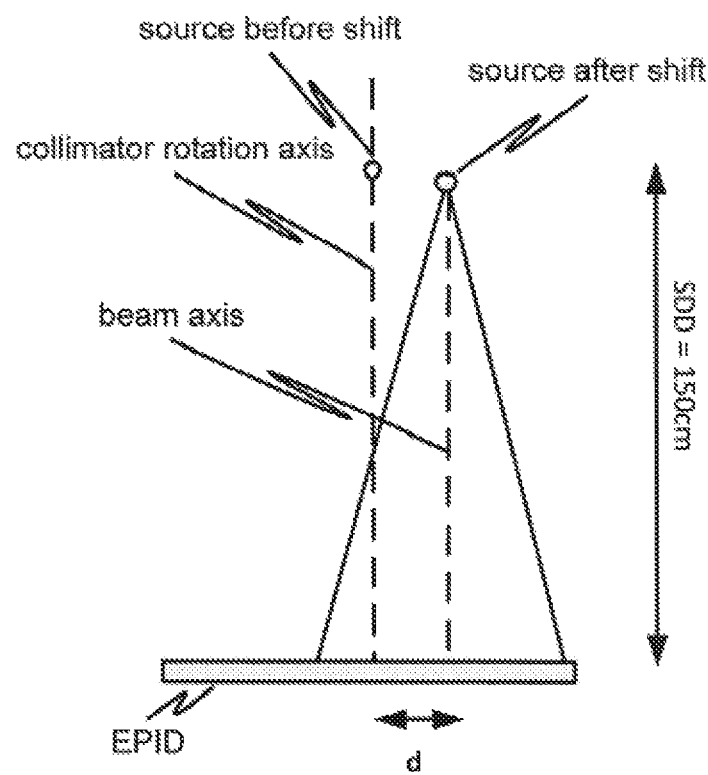
FIG. 11A illustrates a radiation beam axis shifted relative to the collimator rotation axis.
Figure 11B:
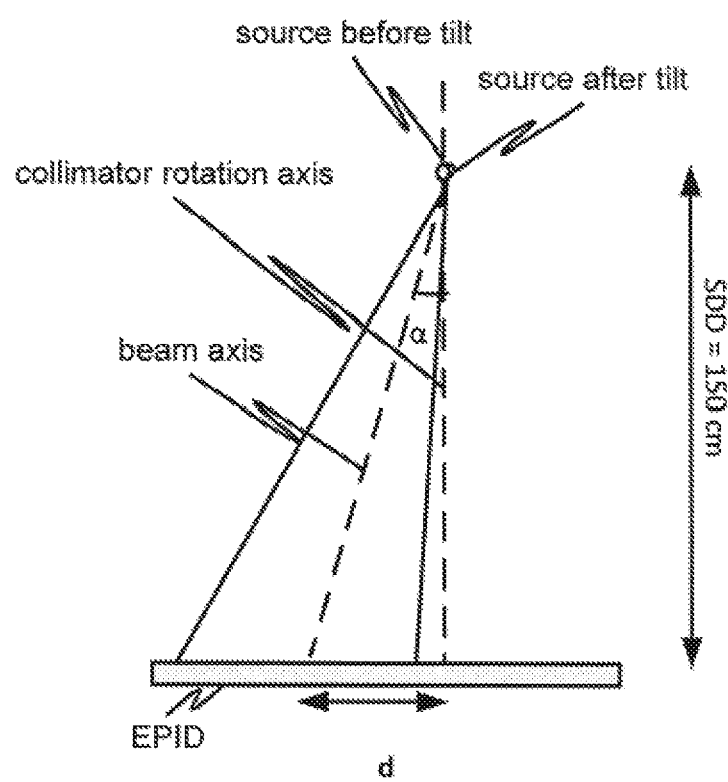
FIG. 11B illustrates radiation beam axis tilted relative to the collimator rotation axis.

If the electron beam does not hit the target 118 orthogonally, it will create an asymmetric radiation beam when looking at a flattened or un-flattened beam (i.e., no flattening filters 117 present). Depending on the system, there are many other sources causing an asymmetric radiation beam. An asymmetric beam may introduce errors in the radiation beam delivered onto the patient. Since the angle of incidence of the electron pencil beam onto the X-ray target 118 is adjusted by adjusting the angle steering coils in the radial and transverse directions, the angle steering coils of the radiation treatment device 103 are calibrated in the radial and transverse angles so that the electron pencil beam hits the X-ray target 118 at a perpendicular angle, or the guide is mechanically adjusted. When the X-ray hits the target 118 at a perpendicular angle, the angle between the collimator rotation axis and the radiation beam spot on the target is zero, as shown in FIG. 10. If the angle between the radiation beam spot on the target and the collimator rotation axis is not zero, the intersection of the beam axis with the imager is offset, as shown in FIG. 11B. If it is determined that the beam is not properly aligned, a signal is sent to the controller 120 to automatically adjust the angle steering coils in the radial and transverse directions.

Determination of Radial and Transverse Beam Offsets

Using the EPID 112, the radial and transverse beam offsets can be measured by determining the beam center at two different elevations of a collimator using distal and proximal leaves and the difference between the centers determined. If there is a difference between the two centers, the difference is attributed to the radial and transversal radiation source offsets.

Determination of Beam Tilt

Generally, radiation tilt is determined indirectly by attributing the asymmetry of a beam profile to tilt, even though asymmetric beam profiles can be due to beam shifts or beam tilts. The accuracy of this indirect tilt measuring method is therefore not optimal.

In the present embodiment, a process S300 is disclosed by which the EPID 112 is used to accurately measure tilt directly. Beam tilt can be determined using:

$$\sin\alpha = \frac{d}{SDD} \qquad (19)$$

where d is the distance between the intersection of the beam axis with the EPID and the projection of the source on the imager (along the collimator rotation axis); SDD is the distance between the radiation source and the EPID; and a is the angle between the beam axis and the collimator rotation axis, as shown in FIG. 11B. When the beam is tilted, a non-zero angle α is formed between the beam axis and the collimator rotation axis. In order to determine the tilt angle, the distance d the between the intersection of the beam axis with the imager and the projection of the source on the imager needs to be determined.

1. Intersection of Beam Axis with Imager

Figure 12:
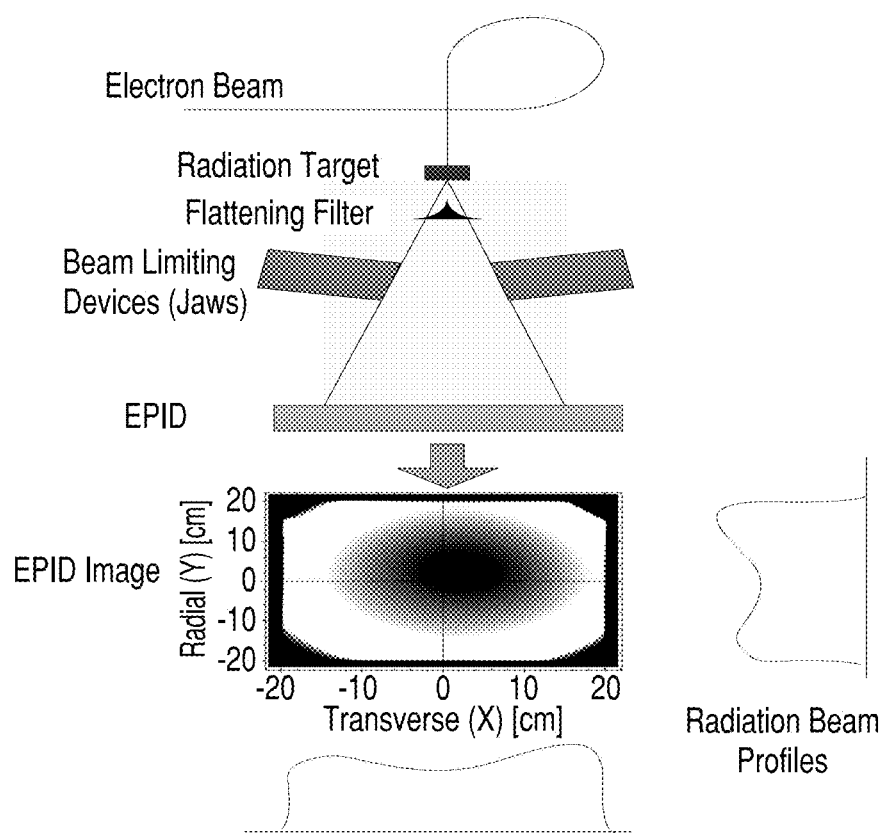
FIG. 12 illustrates an exemplary radiation beam profile generated by a radiation beam.

For a perfectly aligned beam and a perfectly aligned imager, the pixel values $p_i$ of the pixels i of the EPID show a circular beam shape B(r) as perceived by an EPID at location (x, y) on the EPID plane, if the pixel gain $g_i$ is the same for all pixels, as shown in FIG. 12. The relationship between the pixel values and the beam shape is expressed as:

$$p_i = g_i B(r) \qquad (20)$$

with r being the radius of the circular beam.

The beam shape, however, depends on the electron energy E. Calculating the ratio $q_i$ of the pixel values of pixels i at two energies $E_1$ and $E_2$ depicts a circular shape centered at the intersection of the beam axis with the imager, independent of the pixel gains $g_i$:

$$q_i = \frac{B(r; E_1)}{B(r; E_2)} \qquad (21)$$

When the beam is tilted, a non-zero angle α is formed between the beam axis and the collimator rotation axis. This results in the shift of the center of the beam shape as well as a slight distortion of the shape, making it slightly elliptical.

Further, a slight tilt of the EPID with respect to the collimator rotation axis also results in a slight scaling of the distance d, as well as a slight distortion of the beam shape, making it slightly elliptical. However, even if the EPID is tilted, a perfect beam alignment (i.e., an angle α equal to zero) still corresponds to a distance d equal to zero.

In order to determine the center of the elliptical beam shape, the centroid of a circular shape representing the ROI pixels having a known center is calculated using any of the applicable centroid calculation methods. A radial weighting function can also be used during centroid calculation to address ROI truncation artifacts. The distance between the known center (projection of beam source center) and the centroid is then minimized to find the center of the elliptical shape. Once the center of the elliptical shape is determined, the distance d can be determined by measuring the distance between the calculated center of the elliptical shape and the location of the projection of the beam source on the EPID along the collimator rotation axis.

2. Calculation of Beam Tilt

Once d is known, the tilt angle can be determined by taking the inverse of the sine function:

$$\alpha = \arcsin(d/SDD) \quad (22)$$

Figure 13:
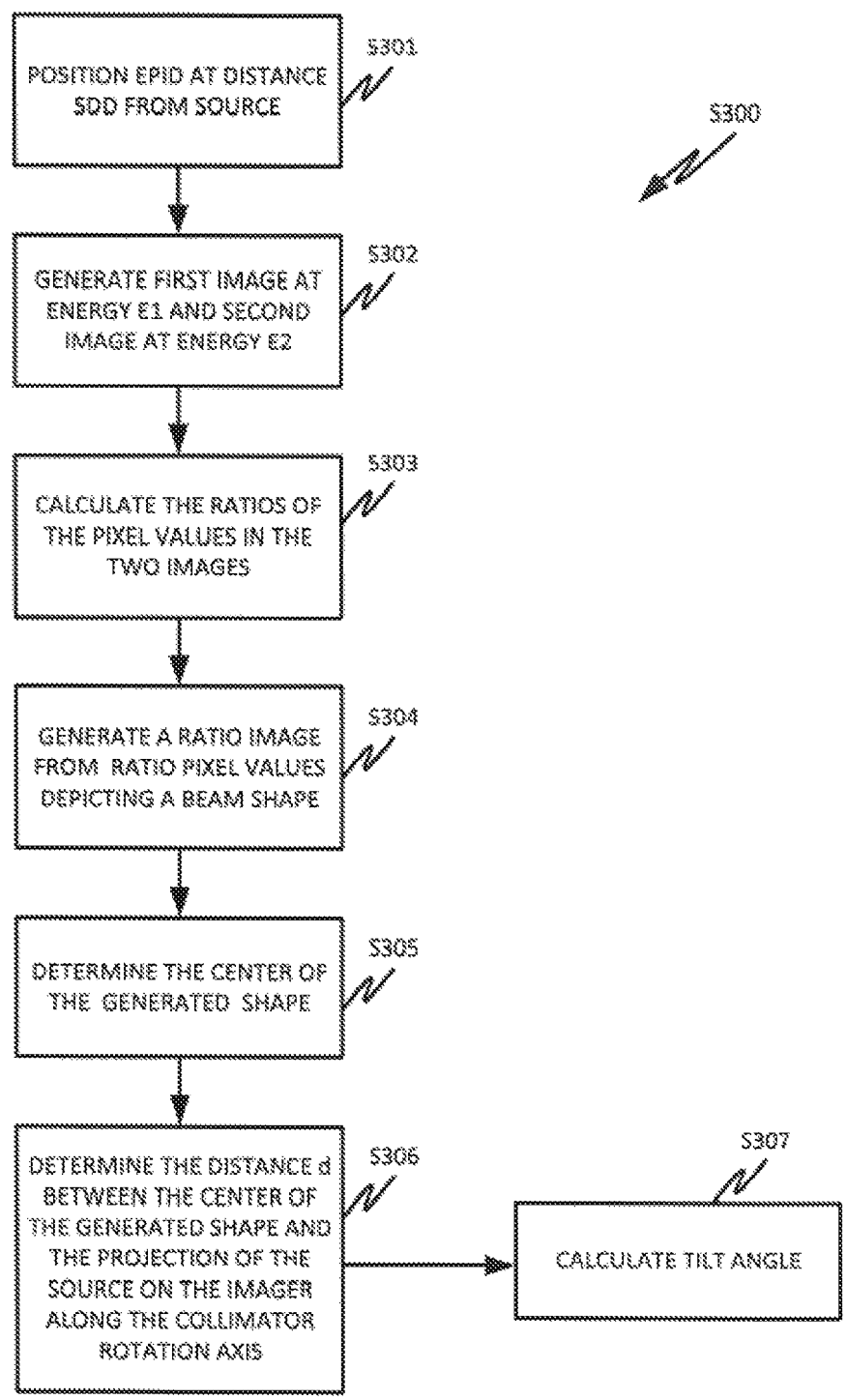
FIG. 13 illustrates an example flow diagram for measuring radiation beam tilt using an EPID.

Accordingly, the beam tilt angle can be determined using an EPID by implementing a process S300 as shown in FIG. 13 that changes the electron energy and uses the ratio of two images to depict the intersection of the beam axis with the EPID. The process S300 is as follows: In step S301, the EPID is positioned at a known distance SDD from the radiation source. The distance SDD could be about 150 cm, for example. The EPID is then irradiated with a radiation beam having a first energy $E_1$ to generate a first image, and with a second radiation beam having a second energy $E_2$ to generate a second image (S302). The second energy can be slightly different than the first energy, and the change need not involve a change of the target and/or flattening filters. Then, for each pixel i, the ratio of the pixel value $p_{i1}$ in the first image and the pixel value $p_{i2}$ in the second image is calculated (S303). Next, a beam shape or beam ratio shape is generated in S304 from the obtained pixel ratios. In S305, the center of the generated shape is determined using any applicable centroid determination methods. Once the center of the generated shape is located, the distance between the location of the center of the shape and the projection of the beam source on the EPID along the collimator rotation axis, is measured (S305). From the measured distance d and the known EPID to source distance (SDD), the tilt angle is calculated using $\alpha = \arcsin(d/SDD)$, where "arc sin" is the inverse of the sin function.

The angle $\alpha$ can also be translated into a photon fluence asymmetry $\Delta$ for a field size s at the isocenter using:

$$\Delta = \frac{(SAD + s\sin\alpha)^2}{SAD^2 - 1} \approx \frac{2s\sin\alpha}{SAD} \quad (23)$$

As disclosed, embodiments use the distance between the intersection of the beam axis with the EPID and the projection of the focal spot on the EPID to measure beam alignment using an EPID without having to implement complex calibration procedures, since the beam alignment determination is made independent of the pixel gains.

Thus, according to described embodiments, the EPID can be used to measure directly the tilt of the radiation beam relative to the collimator rotation axis without implementing complex calibration procedures. The EPID used this way is insensitive to mid-term and long-term pixel gain changes, and it outperforms the accuracy of the current gold standard (water phantom) by an order of magnitude.

EPID as Energy Change Measuring Device for (FFF) Beams

Currently, measuring energy using water phantom scans or special phantoms (typically wedges) in combination with ion chamber arrays is state of the art. However, energy measurements based on water phantom scans or ion chamber arrays require careful setup and alignment. Although EPIDs have also been used as relative measurement devices for beam energy measurements, the EPIDs require elaborate calibration procedures. Also, the currently available calibration procedures do not include correlations with energy changes.

Embodiments described herein disclose systems and methods for using EPIDs as measurement devices for beam energy changes, without requiring elaborate calibration procedures, since the beam energy change determination is made independent of the pixel gains. This is based on the understanding that the flattening filter free (FFF) beam shape B as perceived by an EPID at location (x, y) on the EPID plane, off from penumbra, can be approximated by a Gaussian function:

$$B(x,y) = a \cdot \exp(-c \cdot ((x-x_0)^2 + (y-y_0)^2)) \quad (24)$$

where a is the overall scaling parameter that depends on the beam output which in turn depends on many different parameters, c is the curvature parameter that depends on the electron energy of the beam, and $x_0$ and $y_0$ are the coordinates of the beam center on the EPID plane and depend on the electron beam position and tilt.

The actual pixel response $p_i$ of a pixel i at location (x, y) on the EPID additionally depends on the pixel gain gi:

$$p_i = g_i \cdot B(x,y) \quad (25)$$

where B(x, y) provides the beam shape B as perceived by an EPID at location (x, y) on the EPID plane, (x, y) being the coordinates of pixel i on the EPID plane.

If B' is the beam shape perceived by the same EPID under a different beam condition (e.g., with a different beam energy), then:

$$B'(x,y) = a \cdot \exp(-c' \cdot ((x-x'_0)^2 + (y-y'_0)^2)) \quad (26)$$

$$p_i' = g_i \cdot B'(x,y) \quad (27)$$

Calculating $\rho_i$ as the log of the ratio of the pixel values at these different beam conditions leads to:

$$\rho_i = \log(p_i/p_i') = (c'-c) \cdot (x^2+y^2) + d_1 \cdot x + d_2 \cdot y + d_3 \quad (28)$$

Figure 14:
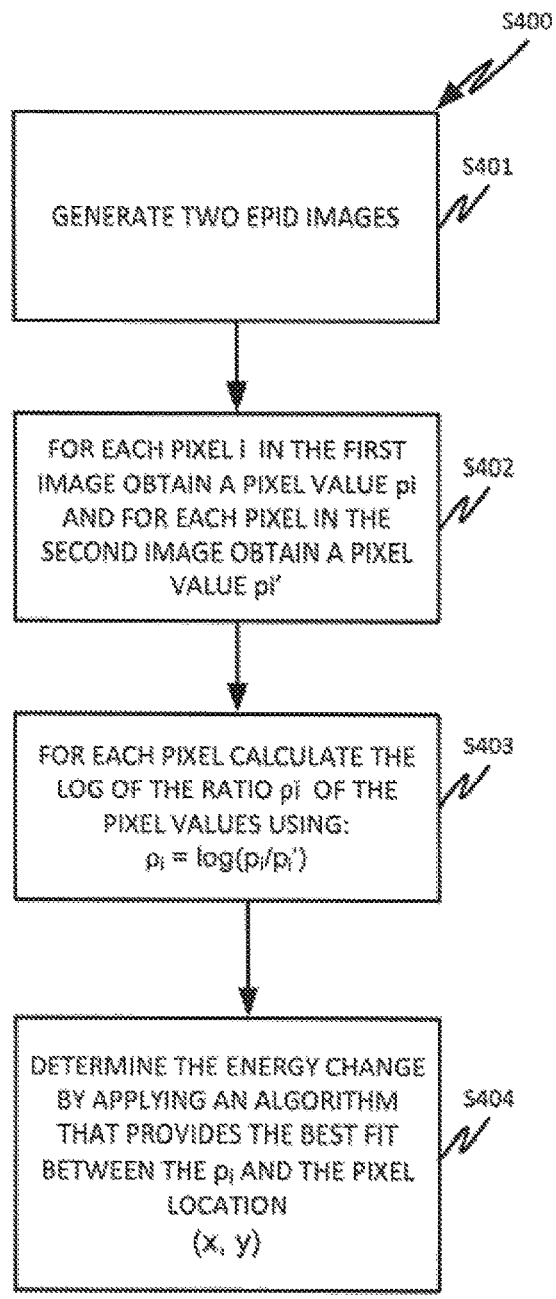
FIG. 14 illustrates an example flow diagram for measuring energy changes using an EPID.

While the parameters $d_1$, $d_2$, and $d_3$ are functions of a, a', c, c', $x_0$, $x_0'$, $y_0$, and $y_0'$, the factor of the quadratic term $(x^2+y^2)$, depends only on the difference of the curvature parameters (c'-c). Thus, the quadratic term $(x^2+y^2)$ depends solely on the difference of the electron energies of the two beam configurations. Therefore, by discarding $d_1$, $d_2$, and $d_3$ and correlating (c'-c) with the energy change, the energy change can be determined. The process S400 for performing energy change measurements of (FFF) beam is shown in FIG. 14 and includes the following steps: In step S401, two EPID images are generated. In step S402, for each pixel i in the first image, the pixel value $p_i$ is determined by measuring the pixel signal, and for each pixel i in the second image, the pixel value $p_i'$ is determined by measuring the pixel signal. Next, for each pixel i, the log of the ratio of the pixel values $\rho_i$ in the two images is calculated using $\rho_i = \log(p_i/p_i')$ in S403. Since $\rho_i$ is related to the change in energy as:

$$\rho_i = \log(p_i/p_i') = (c'-c) \cdot (x^2+y^2) + d_1 \cdot x + d_2 \cdot y + d_3$$

where $(x^2+y^2)$ represents the position of the pixel in the EPID pixel panel, substituting (c'-c) with do gives:

$$\rho_i = d_0 \cdot (x^2+y^2) + d_1 \cdot x + d_2 \cdot y + d_3. \quad (29)$$

Since (c'-c) depends on the electron energy change, $d_0$ also depends on the energy change. Therefore, by determining $d_0$, the energy change can be determined (S404). In order to do so, first a least-squares fit is performed to find the values of $d_0$, $d_1$, $d_2$, and $d_3$ that provide the best fit to:

$$\rho_i = d_0 \cdot (x^2+y^2) + d_1 \cdot x + d_2 \cdot y + d_3$$

over the pixels, where (x, y) are the coordinates of a pixel i on the EPID plane.

Least-squares fitting is a method of finding the best fitting curve to a given set of points by minimizing the sum of the squares of the offsets (e.g., residuals) of the points from each of a set of candidate curves. An application of the least-squares fitting is curve fitting where a curve or a mathematical function is constructed as the best fit to a series of data points, possibly subject to constraints. Curve fitting may be performed through any known methods used in statistical packages such as R and numerical software, for example.

In order to estimate the values $d_0$, $d_1$, $d_2$, and $d_3$ to provide the best fit to:

$\rho_i = d_0 \cdot (x^2+y^2) + d_1 \cdot x + d_2 \cdot y + d_3$, a curve fitting is performed for the given set of pixels i, and $\rho_i$ value for each pixel i at location (x, y). As the relation is linear with respect to the values $d_0$, $d_1$, $d_2$, and $d_3$, any linear regression approach can be applied. Alternatively any non-linear and/or iterative algorithm, for example the Levenberg-Marquardt algorithm, can be used. This can be done by starting with initial values for $d_0$, $d_1$, $d_2$, and $d_3$ which values may be chosen based on previously performed calibration tests. Then, at each iteration, and for each pixel i, the parameter values $d_0$, $d_1$, $d_2$, and $d_3$ are used to calculate the per pixel residual values using:

$$R_i = p_i - d_0 \cdot (x^2+y^2) + d_1 \cdot x + d_2 \cdot y + d_3 \quad (30)$$

The sum R of the squares of the residual values $R_i$ of all pixels i is calculated next and compared to a previously obtained value of this sum. Subsequently, the parameter values $d_0$, $d_1$, $d_2$, and $d_3$ are adjusted to reduce R. For example, the Levenberg-Marquardt (L-M) algorithm may be used to adjust the parameter values $d_0$, $d_1$, $d_2$, and $d_3$ in the iterative procedure. This algorithm combines the Gauss-Newton method and the steepest descent method, each of which could also alternatively be used to adjust the parameter values $d_0$, $d_1$, $d_2$, and $d_3$. When the change in R in two successive iterations is small enough (compared with a tolerance value), the fitting procedure is assumed to have converged. At this point $d_1$, $d_2$, and $d_3$ can be discarded. Any other best fit process can also be applied. The adjusted parameter $d_0$ represents the parameter value satisfying $\rho_i = d_0 \cdot (x^2+y^2)$. Thus, the adjusted parameter value represents (c'-c), which is dependent on the electron energy. As such, the adjusted parameter value can be correlated with the energy change.

In order to correlate the adjusted parameter value with the energy change, the $\rho_i$ value is calculated over many pixels (several 100,000). This typically allows determining changes of $\rho_i$ in the order of 0.001 per 10 cm field size. This corresponds to energy changes in the order of 10 keV. This energy change has been determined based on Monte Carlo simulations made using monoenergetic 6 MeV and 5.5 MeV electron beams and a low-energy target on a 6 MeV magnetron-based machine, where amplitude changes in the order of 0.5% were obtained for the high voltage power supply using the calculated value for $\rho_i$.

In an alternative embodiment, the energy change determination method can also be applied to flattened photon beams. The flattening filter (FF) in this case is considered to be part of the EPID and implicitly included in the pixel gains.

EPID as Beam Flatness and Beam Symmetry Change Measuring Device

The above described algorithm for energy change determination can also be used to determine beam flatness and symmetry change. For example, referring again to: $\rho_i = \log(p_i/p_i') = (c'-c) \cdot (x^2+y^2) + d_1 \cdot x + d_2 \cdot y + d_3$ for a first beam with curvature c and a beam center at $x_0$ and $y_0$ and a second beam with curvature c' and a beam center at $x_0'$ and $y_0'$, the parameters $d_1$ and $d_2$ depend in principle on both electron energies (which affect the curvature parameters c and c') and beam centers:

$$d_1 = 2c'x_0' - 2cx_0 \quad (31)$$

$$d_2 = 2c'y_0' - 2cy_0 \quad (32)$$

Figure 15:
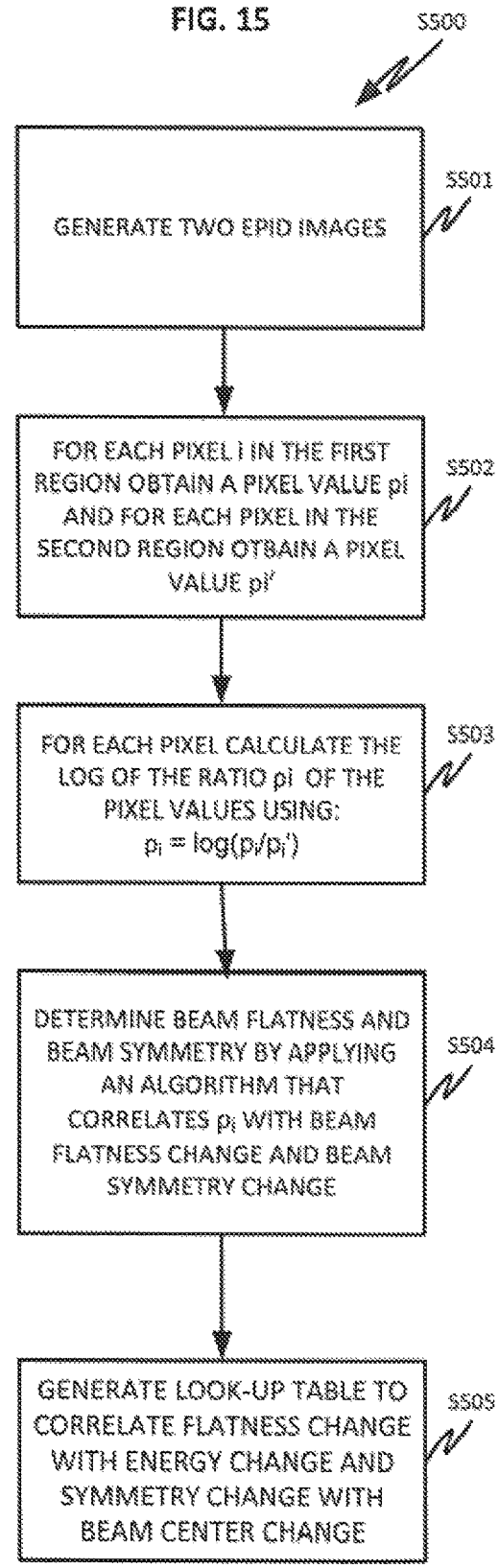
FIG. 15 illustrates an example flow diagram for measuring beam flatness and beam symmetry changes using an EPID.

Accordingly, $d_1$ and $d_2$ are zero if the beam center does not change between the two beams (i.e., $x_0 = x_0'$ and $y_0 = y_0'$). Also, $d_1$ and $d_2$ are proportional to the beam center shift (i.e., $(x_0'-x_0, y_0'-y_0)$) if the beam energy does not change (i.e. c=c'). Furthermore, for realistic energy changes which are relatively small, $d_1$ and $d_2$ are predominantly proportional to the beam center shift (i.e. $(x_0'-x_0, y_0'-y_0)$). Accordingly, beam flatness and beam symmetry changes can be determined by implementing the following process S500 as shown in FIG. 15: In step S501, two images are generated using the EPID. In each image, a region of pixels is selected in the central part of the image (S502), the region being off of the penumbra of for example an 18 cm×18 cm field. For example, each region can be a region including 512×512 pixels corresponding to a field size of about 11 cm×11 cm. For each pixel i in each region, the respective pixel values $p_i$ and $p_i'$ are determined in S502. Then, in step S503, for each EPID pixel i in the region, $\rho_i$, which is the log of the ratio of the pixel values of pixel i in the two images is calculated using:

$\rho_i = \log(p_i/p_i')$, thus providing a ratio image of the two images. Changes in the beam flatness and beam symmetry are next calculated (S504) using the following steps and algorithms: First, a least-squares fit is used to find the values of $d_0$, $d_1$, $d_2$, and $d_3$ that provide the best fit to:

$\rho_i = d_0 \cdot (x^2+y^2) + d_1 \cdot x + d_2 \cdot y + d_3$, over the pixels in the region of pixels, where (x, y) are the integral coordinates of each pixel i on the EPID plane. Then parameter $d_0$ is converted into a flatness change over a reference length L according to:

$$\tilde{d}_0 = \exp(d_0 \cdot L^2) \text{ and} \quad (33)$$

$$\Delta_{Flatness} = 2 \cdot \frac{\tilde{d}_0 - 1}{\tilde{d}_0 + 1} \quad (34)$$

and parameters $d_1$ and $d_2$ are converted into a symmetry change over a reference length L according to:

$$\tilde{d}_1 = \exp(d_1 \cdot L) \quad (35)$$

$$\Delta_{Symmetry\ X} = 2 \cdot \frac{\tilde{d}_1 - 1/\tilde{d}_1}{\tilde{d}_1 + 1/\tilde{d}_1} \quad (36)$$

$$\tilde{d}_2 = \exp(d_2 \cdot L) \quad (37)$$

$$\Delta_{Symmetry\ Y} = 2 \cdot \frac{\tilde{d}_2 - 1/\tilde{d}_2}{\tilde{d}_2 + 1/\tilde{d}_2} \quad (38)$$

Parameter $d_3$ is discarded.

The reference length L can be chosen to correspond to 5 cm at isocenter, for example, but any other length may be used. With the above definitions, this leads to the following intuitive evaluation values, independent of machine parameters:

A flatness change of 1% corresponds to superimposing a change that varies 1% from the center to the outside, over a diameter of 10 cm.

A symmetry change of 1% corresponds to superimposing a change that varies 1% from one edge to the other, over a length of 10 cm.

By means of a series of measurements, the flatness change can be correlated with energy change. For example, a look up table or function may be derived based on the flatness changes for known energy changes (S505). Accordingly, the look up table or function may be subsequently used to estimate an unknown energy change from a derived flatness change.

By means of a series of measurements, the symmetry change can be correlated with beam center change. For example, a look up table or function may be derived based on the symmetry changes for known beam center changes (S505). Accordingly, the look up table or function may be subsequently used to estimate an unknown beam center change for a measured symmetry change. Assuming that either the shift or the tilt is constant, the correlation can be translated to a change in the shift or the tilt, as well.

System Calibration Using EPID

Figure 16:
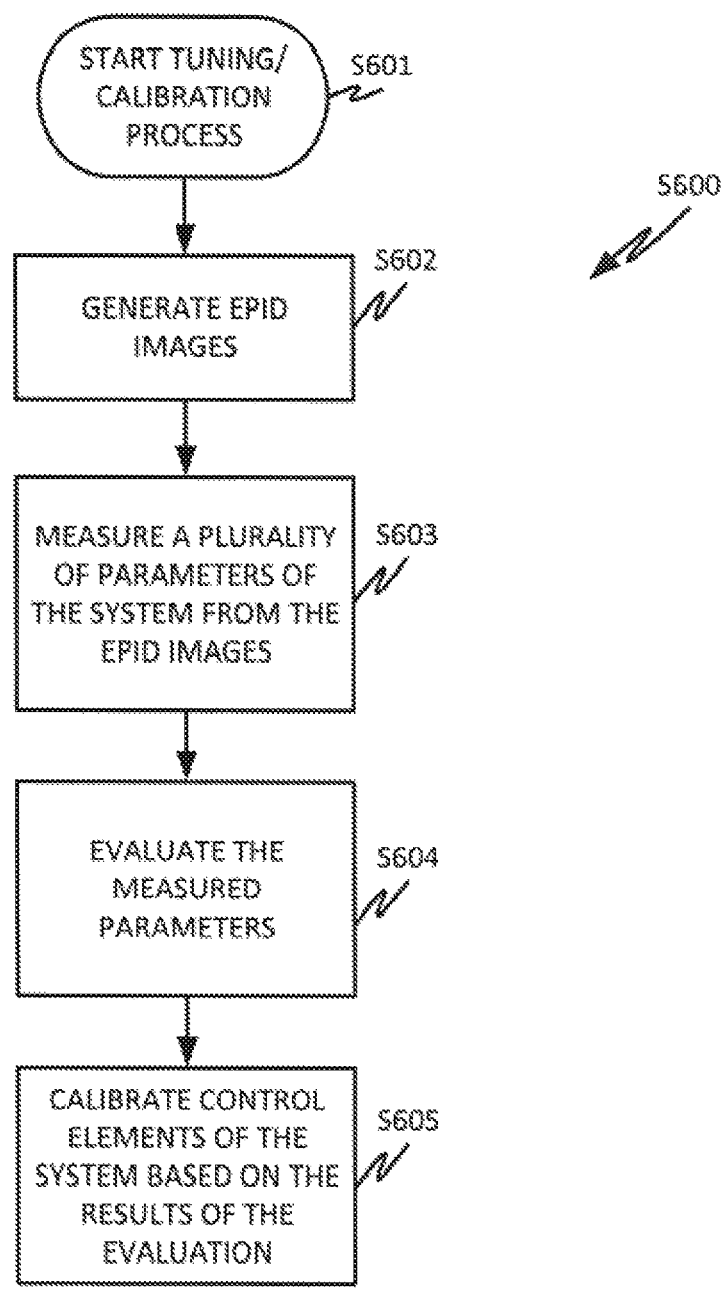
FIG. 16 illustrates an example flow diagram for a calibration process using an EPID.
Figure 17:
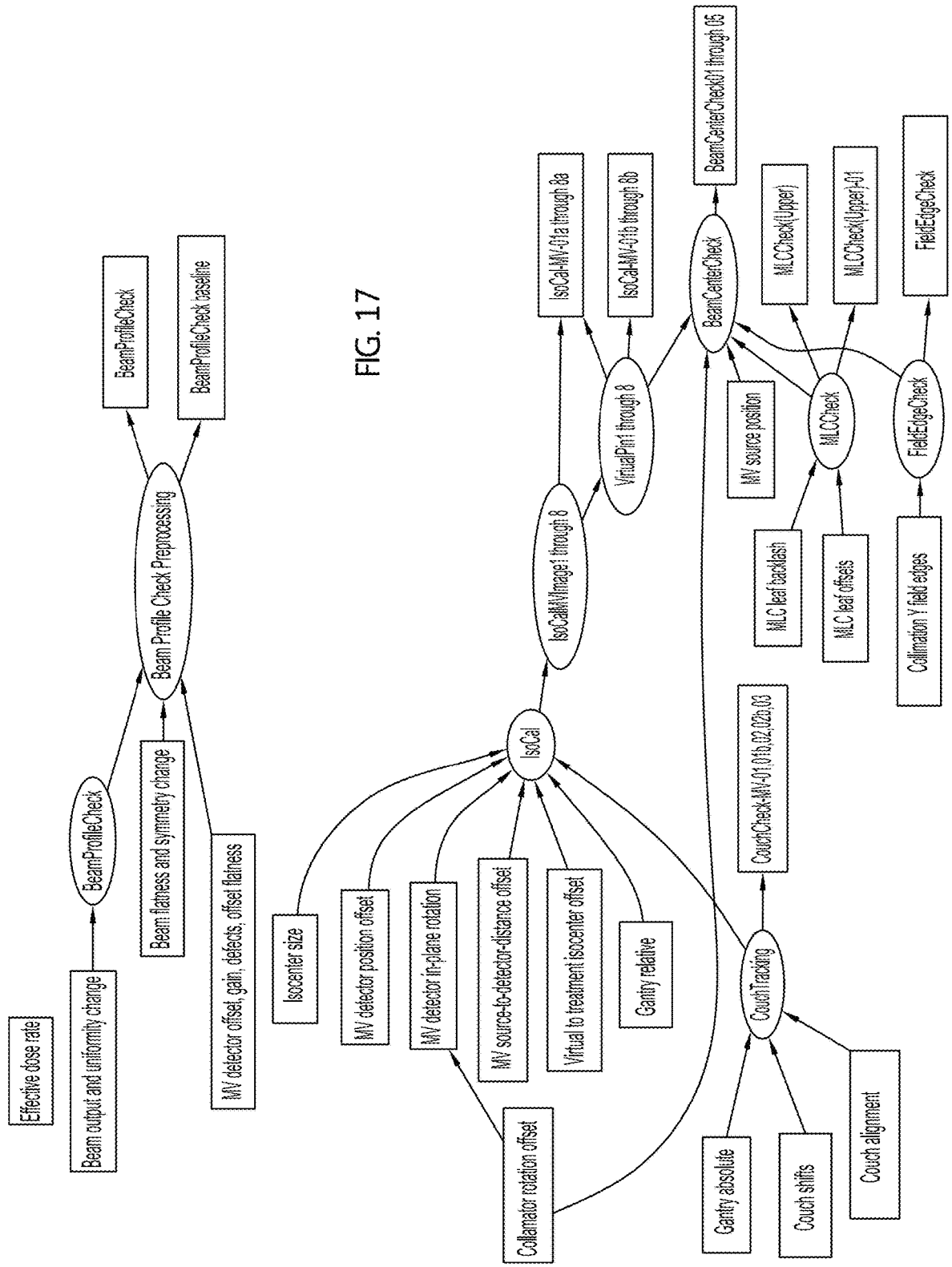
FIGS. 17 and 18 illustrate example flow diagrams for implementations according to embodiments.
Figure 18:
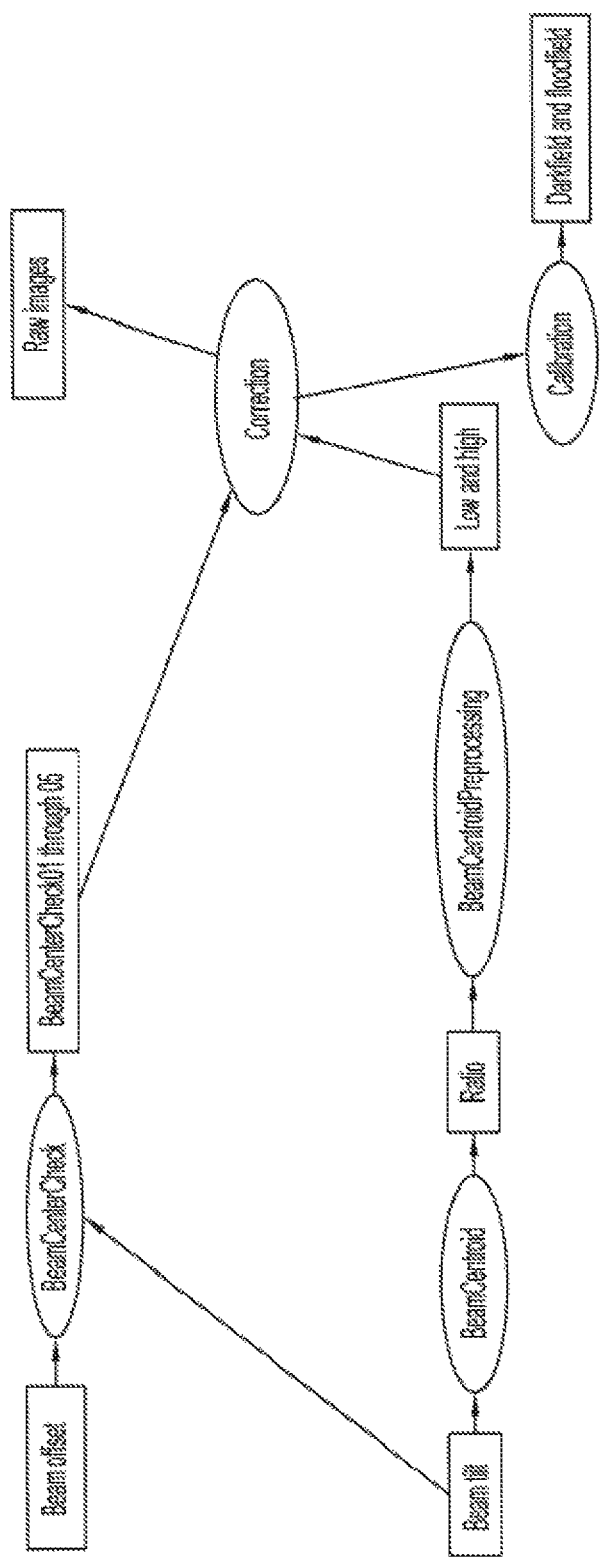

An exemplary automatic tuning/calibration process S600 by which the system 100 is tuned/calibrated with an EPID to operate within expected parameters is shown in FIG. 16. The process S600 includes measuring, using an electronic portal imaging device (EPID) (S602), a plurality of parameters/characteristics of the radiation therapy system 100 (S603), evaluating the measured parameters/characteristics against predetermined standards (S604), and tuning/calibrating the control elements of the system 100 (S605) based on the results of the evaluation so as to ensure that the dosimetric characteristics and the mechanical and geometric integrity of the radiation treatment device 103 is maintained. Process S600 includes steps which use the EPID to measure changes in the energy of the radiation beam, and radiation beam alignment (radial, transverse, and tilt) for the corresponding mechanical element calibration/tuning/adjustment. However, there are many more steps for fully tuning a system 100, including calibration/tuning/adjustment of one or more of the: EPID's axis of motion, light source, collimator jaws, steering coils, X-ray filters, bend magnet shunt current value, scattering foil, ionization chamber, and gantry, for example, as shown in FIGS. 17-18.

The calibration process S600 includes a plurality of calibration tasks which could be fully or partially automatically performed using an electronic portal imaging device EPID 112. The starting of the tuning/calibration process S600 can be initiated at the controller 120 in Step S601, or via a second computer adapted to communicate with controller 120 to execute the calibration tests. In one embodiment the process S600 provides for an automated test sequence that quickly acquires images and completes tests to help medical physicists determine that a radiation therapy system is operating within specified parameters prior to treatment.

Using the EPID 112 in the process S600 allows for the determination of beam flatness and symmetry change with respect to a reference (e.g., baseline). The determined discrepancies between the measured beam flatness and symmetry values and the baseline beam flatness and symmetry values could be used to adjust the angle steering coil accordingly.

Figure 19:
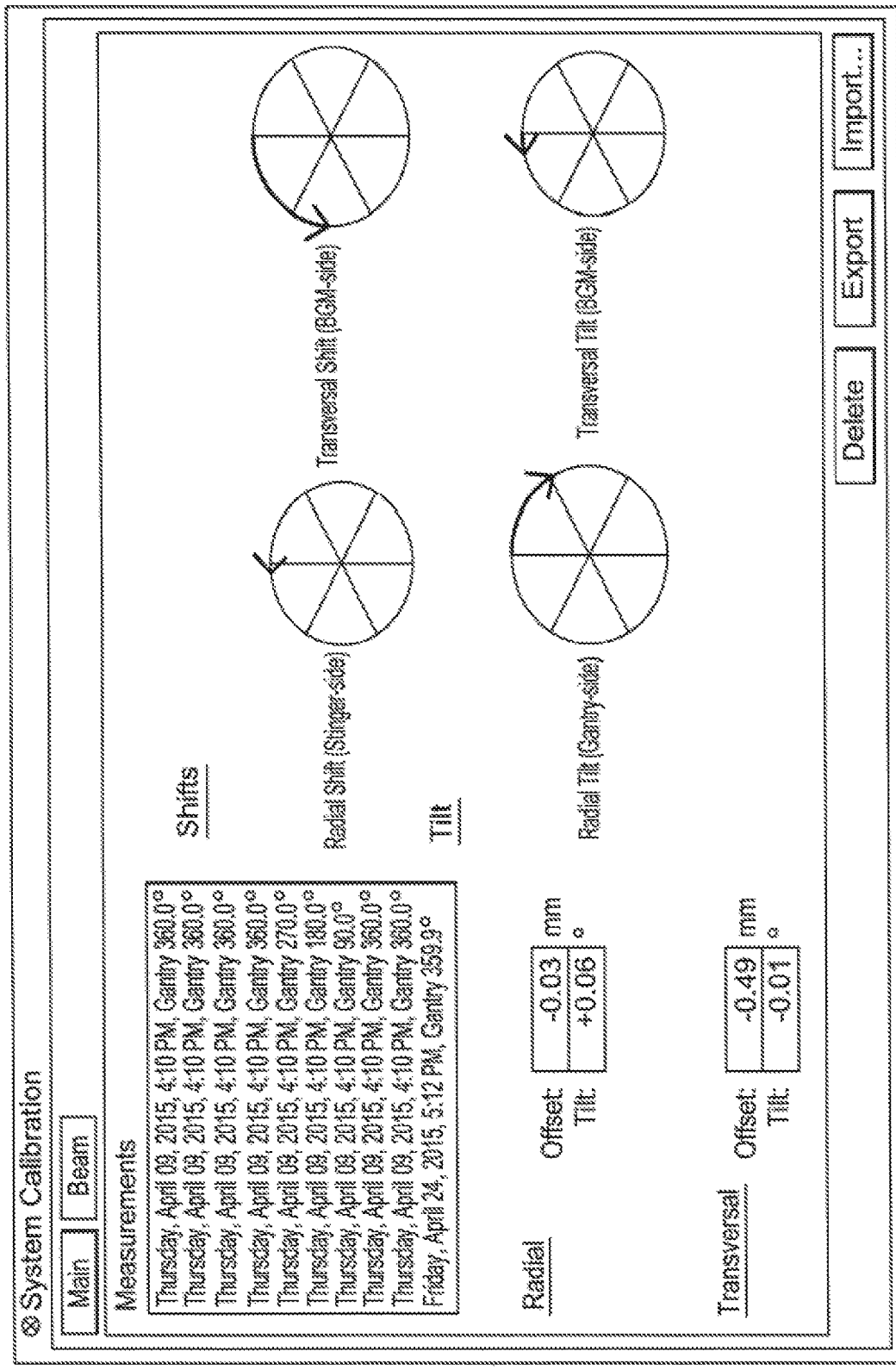
FIG. 19 illustrates an example for graphical indicators for bolt turns to correct misalignment according to an embodiment.

The system calibration process S600 also includes measuring beam tilt and initiating the appropriate calibration of the beam if a determination is made that there is a beam tilt relative to the collimator axis of rotation. The process S600 provides the ability to measure radial and transversal source offset and tilt with gantry at any position. The calibration process S600 also provides the ability to review completed measurements at any time, as well as visual indicators for suggested alignment procedures including alignment bolts correction turns, if the guide is mechanically adjusted, as shown in FIG. 19. Alternatively the angle steering could be adjusted accordingly.

Embodiments described herein therefore provide systems and methods where an EPID can be used as a measurement device for measuring different parameters of the radiation treatment system, without having to implement a complex calibration of the EPID. The general process by which the radiation treatment system and device 103 is automatically calibrated using an electronic portal imaging device (EPID) includes the steps of evaluating various parameters of the radiation treatment device 103, followed by the automatic tuning of various elements of the radiation treatment device in response to the result of the evaluation. This can be achieved by taking one or more images using the EPID 112 by irradiating the EPID 112 with radiation beams (X-rays, electron-beams, etc.) from the LINAC treatment head 110. From the one or more images, a parameter of the radiation treatment device 103 is determined. This parameter can be any one of beam fluence or beam flux, beam symmetry, beam flatness, beam energy, beam linearity, beam dose, beam alignment, light field alignment, etc.

Then each parameter is evaluated to determine whether it falls within a prescribed range. If the parameter falls within a prescribed range, the process steps are repeated to determine and evaluate another parameter of the radiation treatment device 103. If the parameter does not fall within a prescribed range, the output of a control element of the radiation treatment device 103 affecting the respective parameter is adjusted until the parameter falls within the prescribed range. The adjustment can include an adjustment in the radiation limiting (collimating) devices, the angle and position of the steering coils, the location of the flattening filters 117, the size of the bend magnet shunt current, the position of the scattering foils 127, the movement of the EPID arm support 113, the position and symmetry of the ionization chamber 119, and the position of the light source 130, for example. The adjustment can also be done manually, where appropriate. For example, manual adjustment of mechanical screws, bolts, or any other mechanical pieces of the radiation treatment system can be manually done.

This calibration process can be automatically repeated until all parameters of the device are evaluated and the corresponding control element outputs adjusted. Any number of automatic routines using any different type of feedback device can be inserted in the calibration process with the same iterative tuning. When all the outputs are tuned and the parameters fall within prescribed ranges, the radiation treatment device 103 is properly tuned, and the process stops.

FIGS. 17 and 18 illustrate examples of flow diagrams of how the various images, processing steps, and measurement values fit together.

It will be appreciated that the processes, systems, and sections described above can be implemented in hardware, hardware programmed by software, software instruction stored on a non-transitory computer readable medium or a combination of the above. For example, a method for can be implemented using a processor configured to execute a sequence of programmed instructions stored on a non-transitory computer readable medium. The processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C# or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms.

Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, systems, methods, devices, and algorithms for using an EPID as a measuring device for photon count, photon flux, photon fluence, energy changes, beam tilt, beam flatness, and beam asymmetry determination without having to calibrate the EPID. It is thus also apparent that there is provided in accordance with the present disclosure, systems, methods, devices, and algorithms for using an EPID as an imaging device for calibrating a radiation treatment system without needing to implement extensive and complex calibration procedures.

Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A method of determining radiation beam characteristics using an imaging device, the method comprising:
 acquiring one or more images using the imaging device, the imaging device including a plurality of pixels;
 determining one or more parameters from the one or more images; and
 determining one or more characteristics of the radiation beam from the determined one or more parameters,
 wherein the one or more characteristics comprises number of detected photons, radiation beam energy change, radiation beam tilt relative to a collimator axis of rotation, radiation beam symmetry change, radiation beam flatness change, and radiation beam center change,
 wherein the determining of the one or more characteristics is independent of variations in pixel gain values.

2. The method of claim 1, wherein determining the number of detected photons comprises:
 generating a plurality of images;
 measuring pixel values and one or more noise values of a pixel across the plurality of images;
 calculating a mean pixel value of the pixel from the measured pixel values; and
 determining a value corresponding to detected photons per pixel based on the mean pixel value and the one or more noise values for the pixel.

3. The method of claim 2 wherein a value corresponding to detected photons is determined for each pixel of the plurality of pixels.

4. The method of claim 2, wherein the value corresponding to detected photons per pixel is determined using: $N=(p/\sigma)^2$, where N is the number of photons per pixel, p is the mean pixel value, and $\sigma$ is a standard deviation of the pixel across the plurality of images.

5. The method of claim 2, wherein the mean pixel value is determined for a plurality of pixels located in a region of interest (ROI) of an image.

6. The method of claim 5, further comprising normalizing the pixel value using the mean pixel value of the ROI pixels.

7. The method of claim 1, wherein the imaging device is an electronic portal dose imaging device (EPID).

8. The method of claim 1, wherein determining the number of detected photons comprises:
determining a region of interest (ROI) in an image, the ROI including a plurality of pixels;
determining gain compensated pixel values for the plurality of pixels;
measuring noise values for the plurality of pixels;
determining a mean pixel value of the gain compensated pixel values;
determining a value corresponding to detected photons per pixel based on the mean pixel value and the noise values.

9. The method of claim 8, wherein the determining of the gain compensated pixel values for the plurality of pixels includes determining a pixel gain map and correcting each pixel value of the plurality of pixels using the pixel gain map.

10. The method of claim 8, wherein the value corresponding to detected photons per pixel is determined using: $N=(p/\sigma)^2$, where N is the number of photons per pixel, p is the mean pixel value of the gain compensated pixel values, and $\sigma$ is a standard deviation noise value for the pixels in the ROI.

11. The method of claim 1, wherein determining the beam energy change comprises:
generating a first and a second image;
determine a first pixel value for a pixel by measuring pixel signal in the first image, and determine a second pixel value of the pixel by measuring a pixel signal in the second image;
calculate a ratio of the first pixel value to the second pixel value; and
determine a value of a parameter that provides a best fit between the calculated ratio and a pixel location in a pixel panel of the imaging device,
wherein the parameter relates to the beam energy change.

12. The method of claim 11, wherein the best fit value is determined using a least-square fit algorithm.

13. The method of claim 1, wherein determining the beam flatness change and the beam symmetry change comprises:
generating a first and a second image;
determine a first pixel value for a pixel by measuring a pixel signal in the first image, and determine a second pixel value of the pixel by measuring a pixel signal in the second image;
calculate a ratio of the first pixel value to the second pixel value;
determine a plurality of parameter values that provide a best fit between the calculated ratio and a pixel location in a pixel panel of the imaging device; and
determine the beam flatness change and the beam symmetry change based on the determined parameter values.

14. The method of claim 13, wherein a best fit value is determined using a least-square fit algorithm applied to: $\rho=d_0\cdot(x^2+y^2)+d_1\cdot x+d_2\cdot y+d_3$, where $\rho$ is the log of the ratio, (x, y) represents the pixel location along the x and y imaging panel axis, and $d_0$, $d_1$, $d_2$, and $d_3$ are first, second, third and fourth parameters, respectively, wherein applying the least-square fit algorithm includes discarding $d_3$,
the method further comprising converting a first parameter value into flatness change, and converting the second and third parameters into symmetry changes along the x and y axis.

15. The method of claim 13, further comprising correlating the beam flatness change with the beam energy change, and the beam symmetry change with the beam center change.

16. The method of claim 15, further comprising generating a look-up table including correlation values between the beam flatness change and the beam energy change, and between the beam symmetry change and the beam center change.

17. The method of claim 1, wherein determining the radiation beam tilt relative to the collimator axis of rotation comprises:
using the imaging device positioned at a predetermined distance (SDD) from a radiation source, acquiring a first image at a first beam energy, and a second image at a second beam energy;
determining first pixel values by measuring pixel signals for pixels in the first image, and second pixel values by measuring pixel signals for corresponding pixels in the second image;
calculating ratios of the first pixel values to the second pixel values;
generating a ratio image from the calculated ratio pixel values, the ratio image depicting a beam shape;
determining a center of the beam shape;
calculating a distance d between the center of the beam shape and a projection of the radiation source on the imaging device along the collimator axis of rotation; and
determining the radiation beam tilt based on the calculated distance d and the predetermined distance (SDD).

18. The method of claim 17, further comprising calculating the radiation beam tilt relative to a collimator axis of rotation includes calculating a beam tilt angle relative to the collimator axis of rotation using:

$$\sin\alpha = \frac{d}{SDD}.$$

19. The method of claim 18, further comprising translating the calculated beam tilt angle into photon fluence symmetry.

20. The method of claim 1, further including calibrating a radiation treatment device including the imaging device based on the determined one or more radiation beam characteristics.

* * * * *